United States Patent [19]

Shepherd

[11] 4,388,459

[45] Jun. 14, 1983

[54] CERTAIN CINNAMIC ACID OR PROPIOLIC ACID DERIVATIVES

[75] Inventor: Robert G. Shepherd, South Nyack, N.Y.

[73] Assignee: American Cyanamid Company, Stamford, Conn.

[21] Appl. No.: 211,165

[22] Filed: Nov. 28, 1980

Related U.S. Application Data

[62] Division of Ser. No. 8,467, Feb. 1, 1979, Pat. No. 4,259,352.

[51] Int. Cl.³ .................. C07D 213/64; C07C 101/46
[52] U.S. Cl. .................................. 542/427; 562/457; 560/48
[58] Field of Search ........................ 562/457; 542/427

[56] References Cited

U.S. PATENT DOCUMENTS 3,787,478  1/1974  Dolejs et al. ........................ 560/47
3,803,211  4/1974  Dolejs et al. ........................ 560/19

FOREIGN PATENT DOCUMENTS 2128314  1/1972  Fed. Rep. of Germany ...... 424/330
2338819  2/1974  Fed. Rep. of Germany ...... 424/330

*Primary Examiner*—Alan L. Rotman
*Attorney, Agent, or Firm*—Robert P. Raymond

[57] ABSTRACT

This disclosure describes novel 4-[(cycloalkyl or cycloalkenyl substituted)amino, alkylamino or alkenylamino]phenyl compounds, salts and derivatives of these such as cycloalkylamino, cycloalkenylamino, cycloalkyl-alkylamino, cycloalkyl-alkenylamino, cycloalkenyl-alkylamino, and cycloalkyl-cycloalkylamino phenyl compounds and derivatives and suitable salts of these; these compounds are useful as hypolipidemic and antiatherosclerotic agents.

6 Claims, No Drawings

CERTAIN CINNAMIC ACID OR PROPIOLIC ACID DERIVATIVES

This is a division of application Ser. No. 008,467, filed Feb. 1, 1979 now U.S. Pat. No. 4,259,352.

BRIEF SUMMARY OF THE INVENTION

This invention deals with 4-[(cycloalkyl or cycloalkenyl substituted)amino, alkylamino or alkenylamino]phenyl compounds, salts and derivatives of the formula:

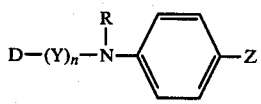

wherein Z is:
(a)

wherein J is selected from the group consisting of hydrogen, loweralkyl, and loweralkyl bearing one or more carboxy, carboloweralkoxy, carbamoyl, acyl, sulfinyl or sulfonyl groups, or (b)

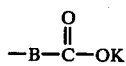

wherein B is a saturated or unsaturated loweralkylene group and K is selected from the group consisting of hydrogen, loweralkyl, loweralkoxyethyl, diloweralkylaminoethyl, (mono- or polyhydroxy)-loweralkyl, (mono or polycarboxy)loweralkyl, (mono- or polycarboxy)hydroxyloweralkyl, allyl, 2,3-epoxypropyl, substituted or unsubstituted (phenyl, benzyl or 3-pyridyl), pyridylmethyl, and tetrahydropyranyl;

R is selected from the group consisting of hydrogen, or a group convertible in vivo thereinto, such as methyl, carboxymethyl, acetyl, succinyl 1-(sodium sulfo)loweralkyl, 1-(sodium sulfo)polyhydroxyalkyl and 1,3-bis-(sodium sulfo)aralkyl;

n is either zero or one;

Y is a divalent radical selected from the group consisting of unbranched or branched $C_1-C_{13}$ alkylene or alkenylene and is either unsubstituted or substituted with at least one $C_1-C_4$ alkyl group;

and D is selected from the group consisting of $C_3-C_{16}$ cycloalkyl or $C_4-C_{17}$ cycloalkenyl and is either unsubstituted or substituted with at least one $C_1-C_{13}$ alkyl, $C_4-C_8$ cycloalkyl, decahydronaphthyl, mechylene, ethylidene, or isopropylidene group;

with the proviso that the total number of carbon atoms in D and Y shall not exceed twenty; and with the further proviso that when n is 1, D is not an unsubstituted cyclopropyl nor a cyclopropyl substituted with at least one $C_1-C_{13}$ alkyl;

and the pharmaceutically acceptable non-toxic acid addition and cationic salts thereof.

Preferred compounds of the invention are as follows: when n is 1, (Formula IA) Y is a divalent radical selected from the group consisting of branched or unbranched $C_1-C_{13}$ alkylene or alkenylene and is either unsubstituted or substituted with at least one $C_1-C_4$ alkyl; D is a moiety selected from the group consisting of $C_3-C_8$ cycloalkyl which is either unsubstituted or substituted with at least one $C_1-C_{13}$ alkyl, a $C_5-C_7$ cycloalkyl, or a decahydronaphthyl group; with the proviso that D is not an unsubstituted cyclopropyl nor a cyclopropyl substituted with at least one $C_1$ to $C_{13}$ alkyl, or (Formula IB) Y is a divalent radical selected from the group consisting of branched or unbranched $C_1-C_{13}$ alkylene or alkenylene; and is either unsubstituted or substituted with at least one $C_1-C_2$ alkyl; and D is a moiety selected from the group consisting of $C_4-C_9$ cycloalkenyl and is either unsubstituted or substituted with at least one $C_1-C_{13}$ alkyl group; and $C_5-C_8$ cycloalkyl unsubstituted or substituted with at least one methylene moiety, and/or at least one $C_1-C_{13}$ alkyl;

and when n is 0, (Formula IC) D is a moiety selected from the group consisting of $C_4-C_7$ cycloalkyl and is either unsubstituted or substituted with at least one $C_4-C_7$ cycloalkyl, and decahydronaphthalene unsubstituted or substituted with at least one $C_1$ to $C_4$ alkyl; or (Formula ID) D is selected from the group consisting of $C_4-C_{16}$ cycloalkyl substituted with at least one $C_1-C_5$ alkyl; or (Formula IE) D is a moiety selected from the group consisting of $C_4-C_{17}$ cycloalkenyl which is either unsubstituted or substituted with at least one $C_1-C_4$ alkyl, and $C_4-C_{10}$ cycloalkyl substituted with a moiety selected from the group consisting of methylene, ethylidene, and isopropylidene and/or at least one $C_1-C_4$; with the proviso that the sum of the number of carbon atoms contained in D and Y in Formula I shall not exceed twenty; and the pharmaceutically acceptable acid addition and cationic salts of the above.

The loweralkyl, loweralkenyl, loweralkynyl, loweralkoxy, loweralkanoyl, and loweralkanesulfonyl groups herein contain 1 to 6 carbon atoms and may be branched or unbranched. The number of hydroxyl groups in the polyhydroxy compounds herein are from 2 to 4 hydroxy groups. The number of carboxy groups in the polycarboxy compounds herein are from 2 to 4 carboxyl groups.

Suitable keto-acids and keto-esters contemplated by the present invention are those in which the group J is selected from the group consisting of carboxymethyl; carboxyethyl; 2-carboethoxy-2-propyl; dicarboethoxymethyl; carboethoxyvinyl and the like. Suitable alkanoic, alkenoic and alkynoic acids and esters are those in which the radical Z is selected from the group consisting of 4-carboxybutyl; 2-carboethoxyethyl; 2-carboxyvinyl; 2-carboethoxyethynyl, and the like.

Preferred compounds of the Formula IA are those wherein Y is a divalent radical selected from those consisting of straight-chain $C_1-C_{13}$ alkylene; and still more preferred are the compounds of Formula IA wherein D is a moiety selected from the group consisting of $C_5$ to $C_8$ cycloalkyl. The most preferred compounds of Formula IA are those where Y is a divalent radical selected from the group consisting of a straight chain $C_6$ to $C_8$ alkylene.

Preferred compounds of Formula IB are those where D is selected from the group consisting of $C_5-C_8$ cycloalkenyl unsubstituted or substituted with at least on $C_1-C_2$ alkyl and Y is a divalent radical selected from the group consisting of $C_1$-$C_{13}$ alkylene; and those compounds wherein Y is a divalent radical selected from the group consisting of $C_4$-$C_{13}$ alkylene and/or D is $C_5$ or $C_6$ cycloalkyl are even more preferred. Additionally preferred embodiments of compounds of Formula IB are those where D is selected from the group consisting of $C_5$ to $C_8$ cycloalkyl substituted with a methylene moiety and/or at least one $C_1$-$C_2$ alkyl, and Y is —$CH_2$— or —$CH(CH_3)$—.

Preferred embodiments of the compounds of Formula IC are those where D is selected from the group consisting of $C_5$-$C_6$ cycloalkyl which is either unsubstituted or substituted with at least one $C_5$-$C_6$ cycloalkyl, and decahydronaphthyl unsubstituted or substituted with at least one $C_1$-$C_4$ alkyl.

Preferred compounds of Formula ID are those where D is selected from the group consisting of $C_4$-$C_{16}$ cycloalkyls which may be unsubstituted or substituted with at least one $C_1$-$C_5$ alkyl and most preferred are those where D is selected from the group consisting of $C_5$ to $C_{12}$ cycloalkyl.

Preferred compounds of Formula IE are those where D is $C_4$-$C_{17}$ cycloalkenyl or $C_4$-$C_8$ cycloalkenyl substituted with at least one $C_{1-4}$ alkyl group; and even more preferred of these is where D is $C_5$-$C_{17}$ cycloalkenyl and even more preferred of these is where D is $C_6$ to $C_{15}$ cycloalkenyl. Other preferred compounds of Formula IE are those where D is $C_4$-$C_{10}$ cycloalkyl substituted with methylene, ethylidene or isopropylidene. Of these the most preferred are those in which D is a $C_5$-$C_{10}$ cycloalkyl substituted with a methylene.

The invention also pertains to novel compositions of matter useful as antiatherosclerotic agents and to methods of ameliorating atherosclerosis by counteracting hyperlipemia and arterial plaque formation in mammals therewith; the active ingredients of said compositions of matter being the novel 4-[(cycloalkyl or cycloalkenyl substituted)amino, alkylamino or alkenylamino]phenyl compounds, salts and derivatives of these of the present invention. These compounds may be utilized either as the free bases or in the form of a pharmaceutically acceptable salt with an organic or inorganic acid or base. The invention also contemplates a method for lowering serum lipids and for ameliorating atherosclerosis in mammals by the administration of said acids and derivatives.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipo-proteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in lesion initiation and development and also, most importantly, whether lesion formation can be prevented or reversed and enlargement of lesions be slowed to stopped. The earliest lesions are now known to be fatty streaks, largely or cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon and Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides had been shown (Carlson and Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et. al. 1974).

The reason for most treatment of hyperlipidemia or hyperlipoproteinemia is for arresting, reversing or preventing atherosclerosis. In the past, attempts have lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine, and nicotinic acid [Levy and Frederckson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Related compounds are the subject of our copending U.S. patent application, Ser. No. 881,457.

DETAILED DESCRIPTION OF THE INVENTION

The compounds of this invention are new and novel 4-[(cycloalkyl or cycloalkenyl substituted)amino, alkylamino or alkenylamino]phenyl compounds, salts and derivatives of these, and have useful biological and pharmacological properties. No hypolipidemic activity has been reported in the literature for these compounds and they are different in structure from other hypolipidemic agents. The compounds of this invention lower serum-lipid concentrations and also minimize atheroma formation in the aorta. These compounds provide the oral administration required of hypolipidemic agents, which patients usually take for many years. The novel compounds of this invention are adequately and reliably absorbed from the gastrointestinal tract with little, if any, gastrointestinal irritation.

I have now found that certain members of this class of compound can safely and effectively lower both serum-sterols and triglycerides in warm-blooded animals. Such actions on serum lipid components are considered to be very useful in the treatment of atherosclerosis, especially in contrast to available drugs whose action is much more limited. For some time it has been considered desirable to lower serum-lipd levels and to correct lipoprotein imbalance in mammals as a preventive measure against atherosclerosis. The compounds of the present invention do not act by blocking late states of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The 4-[(cycloalkyl or cycloalkenyl substituted) amino, alkylamino or alkenylamino]phenyl compounds salts and derivatives of the present invention are, in general, white crystalline solids having characteristic melting points and absorption spectra. They are soluble in organic solvents such as lower alkanols, chloroform, tolune, dimethylformamide, and the like but are generally not very soluble in water.

The novel compounds of the present invention which are organic bases may be converted to their non-toxic acid-addition or cationic salts with a variety of pharmaceutically acceptabale organic and inorganic salt-forming reagents. Thus, acid-addition salts may be formed by admixture of the organic free base in a neutral solvent with one or two equivalents of an acid such as sulfuric, phosphoric, hydrochloric, hydrobromic, trifluoroacetic, citric, tartaric, ascorbic, and the like. Many of the novel compounds of the present invention which contain one or more acidic substituents may be converted to their organic or inorganic cationic salts for therapeutic use. The sodium or potassium salts which are formed in solution in the course of the above described hydrolysis reactions may be isolated as solids by cooling. When it is desirable to purify a compound in the form of the acid, the salt is conveniently formed by treating its solution with exactly one equivalent of base and evaporation or lyophylization. Alkaline earth salts are prepared similarly, often using their acetate salts as a conveniently soluble form. Organic base salts such as those of N-methylglucamine are prepared by dissolving equimolar amounts of the acid and the base in hot ethanol or aqueous alcohols and cooling to crystallization.

Many of the novel compounds of the present invention may be prepared by reaction of a 4-aminophenyl compound with a suitable alkylating agent such as a cycloalkyl halide, sulfate, tosylate, or trifluoromethanesulfonate with or without a sovlent at 30° C. to 150° C. Appropriate 4-aminophenyl compounds are, for example, 4-aminophenylacetic acid; ethyl 4-(aminophenyl)acetate; ethyl 3-(4-aminophenyl)propionate; 4-aminoacetophenone; 4-aminobenzaldehyde; 4-aminocinnamic acid; and methyl 3-(4-aminophenyl)propenoate. Suitable solvents are lower alkanols, N,N-dimethylformamide, N,N-dimethylacetamide, 1,2-dimethoxyethane, acetonitrile, toluene, benzene, hexamethylphosphoramide and the like. The reaction may be carried out with two equivalents of the 4-aminophenyl compound or with one equivalent of the compound plus one equivalent of a base such as an alkali carbonate or bicarbonate or an unreactive organic base such as diisopropylethylamine or alternatively with a catalytic amount of copper powder when a cycloalkyl halide is used as the alkylating agent. Similarly, alkylation of the sodium salt (formed with sodium hydride) of either the amino group of a 4-aminophenyl compound or the anilide moiety of a 4-(acetylamino)phenyl compound yields the novel compounds of the invention or an N-acetyl derivative thereof. Removal of the N-acetyl group by conventional hydrolytic methods affords the desired amino compounds.

Alternative methods of preparation of these compounds are by reductive alkylation of a 4-aminophenyl compound, which may be generated in situ by reduction of a 4-aminophenyl precursor such as a 4-nitrophenyl compound and the like or by a metal hydride reduction of a 4-(acylamino)phenyl compound. For example, 10-cyclopentyldecanal, 7-cyclohexylheptyl ethyl ketone, or another carbonylalkane and ethyl 4-aminophenylacetate are reduced under 1–10 atmospheres of hydrogen using an activated metal catalyst or with a metal hydride such as sodium borohydride forming 4-(10-cyclopentyldecylamino)phenylacetic acid and the like. Diborane reduction of 4-(cycloalkylalkanoylamino)phenyl compounds such as ethyl 4-(11-cyclohexylundecanoylamino)phenylacetate at room temperature or above for 1–6 hours yields the corresponding 4-(cycloalkylalkylamino)phenyl compounds such as ethyl 4-(11-cyclohexylundecylamino)phenylacetate. The 4-(cycloalkylalkanoylamino)phenyl compounds used in these reductions are prepared by acylation of the appropriate 4-aminophenyl compounds with suitable acylating agents, such as cycloalkylalkanoyl halides. To prepare the 4-(substituted-amino)phenyl alkenoic and alkynoic acids it is advantageous to form the corresponding alkylchloroimide from the 4-(acrylamino)phenyl compounds using phosphorus oxychloride and base, and then reduce the alkylchloroimide moiety to an alkylamino group with sodium borohydride.

The 4-(substituted-amino)phenyl compounds of this invention are often prepared from the corresponding p-aminophenyl compounds by the sequence involving esterification of any carboxyl groups present with ethanol or methanol in the presence of boron trifluoride etherate, followed by alkylation of the amino function as described above. The free acids are then liberated by hydrolysis of the ester with aqueous alcoholic sodium hydroxide at 80° for 2–10 hours followed by acidification. The acids obtained by this procedure may be converted to the corresponding cationic salts. For example, the sodium salt may be prepared by reaction of the benzoic acid with sodium hydroxide in a mixture of ethanol and water. Alternatively, the free acids may be prepared by hydrolysis of the corresponding nitriles or various amides, imidates or oxazolines.

The carboxaldehydes of this invention may be prepared by several methods among which is alkylation of the corresponding acetals as described above followed by hydrolysis of the resulting 4-(cycloalkylalkylamino)phenyl compound to the desired aldehyde. Aldehydes may also be prepared by reduction of the appropriate nitriles. For example, treatment of 4-(6-cyclopentylhexylamino)hydrocinnamonitrile with stannic chloride and anhydrous hydrogen chloride gas, followed by hydrolysis in hot water provides 4-(6-cyclopentylhexylamino)hydrocinnamaldehyde. These reductions are also conveniently carried out with hydrides such as diisobutylaluminum hydride.

A method useful for the introduction of the 4-[(cycloalkyl or cycloalkenyl substituted)amino, alkylamino or alkenylamino] group into phenyl compounds is nucleophilic aromatic substitution. An example of this method is the reaction of (cyclohexylmethyl)amine (or the anion derived therefrom by treatment with a strong base) with ethyl 4-fluorobenzoate to yield ethyl 4-[(cyclohexylmethyl)amino]benzoate. In certain instances an amine such as (cyclohexyl)amine may be reacted with a benzyne such as that derived from ethyl 4-bromobenzoate by treatment with sodium amide to yield the 4-(substituted-amino) phenyl compound, in this case ethyl 4-[(cyclohexylmethyl)aminobenzoate.

The α-substituted 4-(substituted-amino)acetophenones of the invention are prepared by reaction of a derivative or the appropriate benzoic acid, such as 4-(11-cyclohexylundeylamino)benzoyl chloride hydrochloride, with two or more equivalents of the reactive salt of an acidic methylene compound, for example the sodium salt of diethylmalonate. Other benzoic acid derivatives are also suitable for this reaction, such as an N-trifluoroacetyl or N-tert-butyloxycarbonyl acid chloride, or a methyl ester of the acid. In some cases the final step in the preparation of the substituted 4-(substituted amino)acetophenones is the removal of the nitrogen-protecting group. In other cases, hydrolysis of one or more of the ester groups in the acylation product affords an unstable polycarboxylic acid which undergoes decarboxylation to allow the preparation of another acetophenone derivative. For example, the reaction of tert-butyl ethyl [4-(11-cyclopentylundecylamino)benzoyl]malonate with trifluoroacetic acid affords ethyl [4-(11-cyclopentylundecylamino)benzoyl]acetate. In other cases, hydrolysis of one or more of the ester groups allows the preparation of the corresponding acid derivative. For example, the hydrolysis of ethyl [4-(6-cyclobutylhexylamino)benzoyl]acetate yields [4-(6-cyclobutylhexylamino)benzoyl]acetic acid.

An alternative procedure for preparing certain α-substituted-4-(substituted-amino)acetophenones is alkylation of the corresponding 4-aminoacetophenone by the methods above. For example, alkylation of methyl 3-(4-aminobenzoyl)propionate with 11-cyclopentylundec-10-enyl bromide yields methyl 3-[4-(11-cyclopentylundec-10-enylamino)benzoyl]propionate. The related carboxylic acids are then obtained by hydrolysis. Certain acids are particularly useful for the preparation of 4-(substituted-amino)phenyl]alkanoic acids by reduction. For example, the Clemmensen or Wolff-Kishner reduction of 3-[4-(6-cyclohexylhexylamino)benzoyl]propionic acid yields 4-[4-(6-cyclohexylhexylamino)phenyl]butyric acid.

The 4-(substituted-amino)phenylalkenoic acids may be prepared by condensation of the appropriate aldehydes or by dehydration of the corresponding substituted-phenylhydroxyalkanoic acids. For example, ethyl 5-[4-(cyclopentylmethylamino)phenyl]-2,4-pentadienoate is obtained by the Wittig reaction of 4-(cyclopentylmethylamino)benzaldehyde with the Wittig reagent, triethyl 4-phosphonocrotonate. Alternatively, these alkenoic acids are obtained by heating 4-[N-(10-cyclopentyldecyl-N-methylamino]benzaldehyde and the like with the sodium salt of the carbanion of ethyl acetate or with a mixture of ethyl acetate, acetic anhydride and potassium acetate. The second method is illustrated by dehydration of ethyl 3-[(cyclohexylmethylamino)phenyl]-3-hydroxypropionate to yield ethyl 4-cyclohexylmethylaminocinnamate.

The acetylenic analogs are prepared by dehydrobromination of the side-chain vic-dibrominated alkanoic acid. For example, dehydrobromination of ethyl 3-[(4-cyclobutylmethylamino)phenyl]-2,3-dibromopropionate, its isomers for N-acyl analogs or of ethyl 3-[(4-cyclobutylmethylamino)phenyl]-3-bromacrylate yields ethyl 4-(cyclobutylmethylamino)phenylpropiolate. The acetylenic acids are also formed from (4-substituted-amino)phenylacetylene metal salts by carboxylation with carbon dioxide. The 4-(substituted-amino)phenylacetylenes are also used by N-acylating with t-butyl azidoformate followed by conversion to the lithium acetylide salt and the subsequent reaction of the lithium salt with boron trifluoride etherate in tetrahydrofuran at −20° C. to form tris-[(4-substituted-alkylamino)-phenylethynyl]boranes. The tetrahydrofuran solution of the borane is in turn reacted with ethyl diazoacetate, followed by water to yield ethyl 4-[(4-monoalkylamino)phenyl]butynoate.

The 4-(substituted-amino)phenylalkanoic acids, or esters are also prepared by catalytic reduction at 1 to 10 atmospheres of hydrogen of the corresponding alkenoic or alkynoic acid derivatives.

The 4-(substituted-amino)phenylalkenoic acids and derivatives are prepared by Friedel-Crafts acylation of the N-acyl-N-alkylanilines with the appropriate dicarboxylic acid anhydride or half acid chloride. The substituted-aminobenzoylalkanoic acids or esters, produced by this and other syntheses, may be converted to the corresponding 4-(substituted-amino)phenylalkanoic acids by reduction with (a) hydrazine and alkali in diethylene glycol at 140° for 3 hours, (b) zinc amalgam and ethanolic hydrochloric acid at 60° for 5 hours, (c) red phosphorus and hydriodic acid, or (d) ketalization with 1,2-ethanedithiol followed by Raney nickel desulfurization. The amides of these 4-(substituted-amino)-phenylalkanoic acids are prepared by heating the corresponding 4-(substituted-amino)phenylalkyl ketones with aqueous alcoholic ammonium polysulfide followed by hydrolysis to yield the acids with the same number of carbon atoms as the ketone. These acids are also prepared by reacting 4-(N-t-butyloxycarbonyl-N-substituted-amino)phenylmagnesium halides with 2-(3-halopropyl)-2-oxazolines, followed by mild acid removal of 2-oxazolinyl and t-butoxycarbonyl protecting groups. Similarly, the above Grignard reagent can be reacted with 3-bromotriethylorthopropionate in the presence of dilithiumtetrachlorocuprate to yield the desired acids after removal of the protecting groups from the amino and carboxyl groups.

In certain cases, the unsaturation is introduced at a late stage of the preparation of the 4-(cycloalkyl unsaturated-alkylamino)benzoic acid derivatives. For example, an alkyl 4-(cycloalkylhaloalkylamino)benzoate is dehydrohalogenated to the corresponding olefinic compound.

Certain derivatives

of the aminobenzoyl nitrogen atom are useful for providing greater solubility, more uniform and reliable intestinal absorption, and for a certain degree of modification of the pharmacology of the compounds of the present invention. Some of these derivatives can be converted to the corresponding N-H forms by the acidity of the stomach or the alkalinity of the small intestine. Others are converted by metabolic processes. The methyl and carboxymethyl derivatives and the like are prepared by the alkylation, reductive alkylation, and acylamino reduction methods above. Derivatives such as the acetyl and succinyl compounds may be prepared using acetyl chloride, acetic anhydride, succinic anhydride, etc. in the presence of pyridine, triethylamine or the like at temperatures moderate enough to avoid acylation of the amide moiety. The 1-(sodium sulfo)alkyl derivatives are obtained by reaction of the 4-(substituted amino)phenyl compound with sodium bisulfite and an aliphatic aldehyde, a polyhydroxyaldehyde such as glyceraldehyde or glucose, or cinnamaldehyde in a mixed organic-aqueous medium. In the case of cinnamaldehyde, the di-sulfonate salts result from addition of the bisulfite to the carbon-nitrogen double bond of the anil intermediate as well as to the carbon-carbon double bond of cinnamaldehyde itself.

The novel compounds of the present invention are not only potent hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active compound, for a subject of about 70 kg. of body weight, are administered in a 24 hour period. This dosage regimen may be adjusted to provide the optimum theraputic response. For example, several divided doses may be administered daily or the dose may be proportionally reduced as indicated by the exigencies of the therapeutic situation. A decided practical advantage of this invention is that the active compound may be administered in a convenient manner by the oral route. The compounds of the present invention exert a more powerful hypocholestermic and antiatherosclerotic effect than the aforementioned adjuvants and synthetic medicaments. It is not known how these novel compounds operate in the blood serum and no theory of why these compounds so operate is advanced. It is not intended that the present invention should be limited to any particular mechanism of action of lowering serum lipids or of ameliorating atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage-unit form contains between about 50 and 250 milligrams of active compound.

The tablets, troches, pills, capsules and the like may also contain the following: a binder such as gum tragacanth, acacia, corn starch or gelatin; excipients such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage-unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propyl parabens as preservatives, a dye, and flavoring such as cherry or orange flavor. Of course, any material used in preparing any dosage-unit form should be pharmaceutically pure and substantially non-toxic in the amounts employed. In addition, the active ingredients may be incorporated into sustained-release preparations and formulations.

The invention will be described in greater detail in conjunction with the following specific examples.

EXAMPLE 1

Preparation of p-[(cyclohexylmethyl)amino]phenylacetic acid

A solution of 6 g. of cyclohexylmethyl bromide and 11.19 g. of ethyl p-aminophenyl acetate in 30 ml. of hexamethylphosphoramide is heated in an oil bath for 20 hours. The solution is poured into ice-cold water and extracted several times with diethyl ether. The combined ether extracts are washed with water, dried with anhydrous magnesium sulfate, and evaporated to dryness under reduced pressure to furnish ethyl p-cyclohexylmethylaminophenyl acetate as an oil.

The oil is dissolved in 250 ml. of ethanol:water (9:1) containing 9 g. of potassium hydroxide and the resulting solution is stirred at the reflux temperature for 3 hours. After chilling, the mixture is acidified with concentrated hydrochloric acid, diluted with water, and extracted twice with methylene chloride. The combined extracts are washed with water, dried with anhydrous magnesium sulfate, and evaporated to dryness under reduced pressure to furnish p-[(cyclohexylmethyl)amino]phenylacetic acid.

EXAMPLES 2-108

Treatment of the indicated halide starting materials set forth in Table I below with ethyl p-aminophenyl acetate followed by saponification according to Example 1 is productive of the corresponding p-[substituted amino]phenylacetic acids listed in Table I.

TABLE I

| Example | Starting material | Product |
|---|---|---|
| 2 | 1-iodomethyl-2-methyl cyclopentane Chem. Abst. 67,90421y | p-[(2-methycyclopentyl)methylamino]phenylacetic acid |
| 3 | -bromomethyl cyclopentane Chem. Abst. 66, 18472c | p-[(cyclopentyl)methylamino]phenylacetic acid |

TABLE I-continued

| Example | Starting material | Product |
|---|---|---|
| 4 | 1-bromomethyl-4-methyl-cyclohexane Chem. Abst. 70,2934b | p-[(4-methylcyclo-hexyl)methylamino]-phenylacetic acid |
| 5 | 1-chloromethyl-2-methyl-cyclohexane Chem. Abst. 68,88671h | p-[(2-methylcyclo-hexyl)methylamino]-phenylacetic acid |
| 6 | 1-(1,2-dimethylcyclo-hexyl)-2-chloropropane Chem. Abst. 73,14272j | p-[1-(1,2-dimethyl-cyclohexyl)-2-propyl-amino]phenylacetic acid |
| 7 | 1-(1,3-dimethylcyclo-hexyl)-2-chloropropane Chem. Abst. 73,14272j | p-[1-(1,3-dimethyl-cyclohexyl)-2-propyl-amino]phenylacetic acid |
| 8 | 1-(1,4-dimethylcyclo-hexyl)-2-chloropropane Chem. Abst. 73,14272j | p-[1-(1,4-dimethyl-cyclohexyl)-2-propyl-amino]phenylacetic acid |
| 9 | α-bromomethylcyclo-heptane Chem. Abst. 51,1049e | p-(cycloheptylmethyl-amino)phenylacetic acid |
| 10 | α-bromomethylcyclo-octane Chem. Abst. 68,104595t | p-(cyclooctylmethyl-amino)phenylacetic acid |
| 11 | α-chloroethylcyclo-pentane Chem. Abst. 72,110862b | p-(1-cyclopentylethyl-amino)phenylacetic acid |
| 12 | 1-bromo-2-cyclo-penytlbutane | p-(2-cyclopentylbutyl-amino)phenylacetic acid |
| 13 | 1-bromo-2-cyclopentyl-hexane Ref. A | p-(2-cyclopentylhexyl-amino)phenylacetic acid |
| 14 | 2-chloroethylcyclo-hexane Chem. Abst. 68,86671h | p-(2-cyclohexylethyl-amino)phenylacetic acid |
| 15 | 1-(2-bromoethyl)-1-ethylcyclohexane Chem. Abst. 70,57233c | p-[2-(1-ethylcyclo-hexyl)ethylamino]phenylacetic acid |
| 14 | 2-chloroethylcyclo-hexane Chem. Abst. 68,86671h | p-(2-cyclohexylethyl-amino)phenylacetic acid |
| 15 | 1-(2-bromoethyl)-1-ethylcyclohexane Chem. Abst 70,57233c | p-[2-(1-ethylcyclo-hexyl)ethylamino]phenylacetic acid |
| 16 | 1-bromo-2-(3-methyl-cyclohexyl)butane Ref. A | p-[2-(3-methylcyclo-hexyl)butylamino]phenylacetic acid |
| 17 | 1-bromo-2-cyclohexyl-pentane Ref. A | p-[(2-cyclohexyl)pen-tylamino]phenylacetic acid |
| 18 | 1-bromo-2-cyclohexyl-butane Ref. A | p-[(2-cyclohexyl)butyl-amino]phenylacetic acid |
| 19 | 1-bromo-2-cyclohexyl-propane Ref. A | p-[(2-cyclohexyl)pro-pylamino]phenylacetic acid |
| 20 | 1-(2-chloroethyl)-2,3-dimethylcyclohexane Chem. Abst. 69,56053n | p-[2-(2,3-dimethylcyclo-hexyl)ethylamino]-phenylacetic acid |
| 21 | 1-(2-chloroethyl)-3,5-dimethylcyclohexane Chem. Abst. 69,56053n | p-[2-(3,5-dimethylcyclo-hexyl)ethylamino]-phenylacetic acid |
| 22 | 2-(2-chloroethyl)-1,4-dimethylcyclohexane Chem. Abst. 69,56053n | p-[2-(2,5-dimethylcyclo-hexyl)ethylamino]-phenylacetic acid |
| 23 | 1-(2-chloroethyl)-2-ethylcyclohexane Chem. Abst. 69,56053n | p-[2-(2-ethylcyclo-hexyl)ethylamino]-phenylacetic acid |
| 24 | 1-(2-chloropropyl)-3-methylcyclohexane Chem. Abst. 67,53405a | p-[1-(3-methylcyclo-hexyl)-2-propylamino]-phenylacetic acid |
| 25 | 1-(2-bromoethyl)-1-methylcyclohexane Chem. Abst. 72,132133s | p-[2-(1-methylcyclo-hexyl)ethylamino]-phenylacetic acid |
| 26 | 1-(2-chloroethyl)-2-methylcyclohexane Chem. Abst. 69,56053n | p-[2-(2-methylcyclo-hexyl)ethylamino]-phenylacetic acid |
| 27 | 1-(2-chloroethyl)-3-methylcyclohexane Chem. Abst. 69,56053n | p-[2-(3-methylcyclo-hexyl)ethylamino]-phenylacetic acid |
| 28 | 1-(2-chloroethyl)-4-methylcyclohexane Chem. Abst. 69,56053n | p-[2-(4-methylcyclo-hexyl)ethylamino]-phenylacetic acid |
| 29 | 2-bromomethylcyclo-heptane Ref. A | p-(cycloheptylmethyl-amino)phenylacetic acid |
| 30 | 3-bromopropylcyclo-butane Ref. A | p-(3-cyclobutyl)propyl-amino)phenylacetic acid |
| 31 | 3-bromopropylcyclo-pentane Chem. Abst. 75,15138f | p-(3-cyclopentyl)propyl-aminophenylacetic acid |
| 32 | 3-bromopropylcyclo-hexane Ref. A | p-(3-cyclohexyl)propyl-amino)phenylacetic acid |
| 33 | 1-(3-chloropropyl)-3-ethylcyclohexane Chem. Abst. 68,12589w | p-[3-(3-ethylcyclo-hexyl)propylamino]-phenylacetic acid |
| 34 | 1-(3-bromopropyl)-3-methylcyclohexane Chem. Abst. 75,151387f | p-[3-(3-methylcyclo-hexyl)propylamino]-phenylacetic acid |
| 35 | 1-(3-bromopropyl)-4-methylcyclohexane Chem. Abst. 75,151387f | p-[3-(4-methylcyclo-hexyl)propylamino]-phenylacetic acid |
| 36 | 1-bromo-3-cyclohexyl-pentane Ref. A | p-[(3-cyclohexyl)pentyl-amino]phenylacetic acid |
| 37 | (2-bromomethyl)butyl-cyclohexane Ref. A | p-[(3-cyclohexyl-2-ethyl)propylamino]phenylacetic acid |
| 38 | 1-[1-bromo-2-methyl-3-(3-etylcyclohexyl]-propane Chem. Abst. 68,12529w | p-[3-(3-ethylcyclo-hexyl)-2-methyl]pro-pylaminophenylacetic acid |
| 39 | 4-bromobutylcyclopentane Chem. Abst. 69,18646z | p-(4-cyclopentyl)-butylaminophenylacetic acid |
| 40 | 4-chlorobutylcyclohexane Ref. A | p-(4-cyclohexyl)butyl-aminophenylacetic acid |
| 41 | 5-bromo-2-cyclohexyl-pentane Ref. A | p-(4-cyclohexyl)pentyl-aminophenylacetic acid |
| 42 | 1-bromo-4-cyclohexyl-hexane Ref. A Chem. Abst. 70,P87143r | p-(4-cyclohexyl)hexyl-aminophenylacetic acid |
| 43 | 1-bromo-4-cyclohexyl-2-ethylbutane Ref. A | p-(4-cyclohexyl-2-ethyl)butylaminophenyl acetic acid |
| 44 | 1-bromo-4-(3-methyl-cyclohexyl)butane Ref. A | p-[4-(3-methylcyclo-hexyl)butylamino] phenylacetic acid |
| 45 | 1-chloro-4-(4-methyl-cyclohexyl)butane Ref. A | p-[4-(4-methylcyclo-hexyl)butylamino] phenylacetic acid |
| 46 | 1-chloro-4-(4-ethyl-cyclohexyl)butane Ref. A | p-[4-(4-ethylcyclo-hexy)butylamino] phenylacetic acid |
| 47 | 1-(4-chlorobutyl)-2,3-dimethylcyclo-hexane Chem. Abst. 70,P87143r; Ref. A | p-[4-(2,3-dimethylcyclo-hexyl)butylamino]-phenylacetic acid |
| 48 | 1-(4-chlorobutyl)-2,5-dimethylcyclo-hexane Ref. A | p-[4-(2,5-dimethyl-cyclohexyl)butyl-amino]phenylacetic acid |
| 49 | 1-(4-chlorobutyl)-4-methoxycyclo-hexane Ref. A | p-[4-(4-methoxylcyclo-hexyl)butylamino]-phenylacetic acid |
| 50 | 1-(4-bromobutyl)-2-methoxycyclo-hexane Ref. A | p-[4-(2-methoxylcyclo-hexyl)butylamino]-phenylacetic acid |
| 51 | 4-bromobutyl)-cycloheptane Ref. A | p-(4-cycloheptyl)butyl-aminophenylacetic acid |
| 52 | 1-(4-chlorobutyl)-4-cyclohexylcyclo-hexane Ref. A | p-[4-(4-cyclohexyl)cyclohexyl]butylamino phenylacetic acid |
| 53 | 2-(4-chlorobutyl)-decahydronapthylene Ref. A | p-[4-(2-decahydronaph-thyl]butylamino phenylacetic acid |
| 54 | 4-bromobutylcyclo-heptane | p-(4-cycloheptyl)-butylamino phenylacetic |

TABLE I-continued

| Example | Starting material | Product |
|---|---|---|
| 55 | 4-chloropentylcyclopropane Chem. Abst. 69,105732t, 74,31488x | p-[5-(cyclopropyl)-2-pentylamino]phenylacetic acid |
| 55 | 4-chloropentylcyclopropane Chem. Abst. 69,105732t, 74,31488x | p-[5-(cyclopropyl)-2-pentylamino]phenylacetic acid |
| 56 | 1-bromo-5-cyclobutylpentane Chem. Abst. 70,P87143r; Ref. A | p-[5-(cyclobutyl)pentylamino]phenylacetic acid |
| 57 | 1-chloro-5-cyclopentylpentane Chem. Abst. 70,P87143r; Ref. A | p-[5-(cyclopentyl)pentylamino]phenylacetic acid |
| 58 | 5-bromopentylcyclohexane Chem. Abst. 55,21016e | p-[5-(cyclohexyl)phenylamino]phenylacetic acid |
| 59 | 5-chloropentylcycloheptane Chem. Abst. 70,P87143r Ref. A | p-[5-(cyclopentyl)pentylamino]phenylacetic acid |
| 60 | 6-chlorohexylcyclopentane Ref. A | p-[6-(cyclopentyl)hexylamino]phenylacetic acid |
| 61 | 6-chlorohexylcycloheptane Chem. Abst. 70,P87143r | p-[6-(cycloheptyl)hexylamino]phenylacetic acid |
| 62 | 1-chloro-7-cyclopentylheptane Chem. Abst. 75,P141605n | p-[7-(cyclopentyl)heptylamino]phenylacetic acid |
| 63 | 8-chlorooctylcyclopentane Ref. A; Chem. Abst. 70,87143r | p-[8-(cyclopentyl)octylaminophenylacetic acid |
| 64 | 8-bromooctylcyclohexane | p-[8-(cyclohexyl)octylaminophenylacetic acid |
| 65 | 1-bromo-8-(3,3,5-trimethylcyclohexyl)octane Chem. Abst. 75,P20026q | p-[8-(3,3,5-trimethylcyclohexyl)octylamino]phenylacetic acid |
| 66 | 9-bromononylcyclopentane Ref. A; Chem. Abst. 70,P87143r | p-[9-(cyclopentyl)nonylamino]phenylacetic acid |
| 67 | 13-bromotridecylcyclopentane | p-[13-(cyclopentyl)tridecylamino]phenylacetic acid |
| 68 | 1-(2-chlorocyclopropyl)pentane Chem. Abst. 75,49270a | p-[2-pentyl)cyclopropylamino]phenylacetic acid |
| 69 | 1-bromocyclopropylpentane Chem. Abst. 75,76195n | p-[1-pentyl)cyclopropylamino]phenylacetic acid |
| 70 | 1-(2-bromocyclopropyl)butane Chem. Abst. 74,124924b | p-[2-butylcyclopropyl)amino]phenylacetic acid |
| 71 | bromocyclopentane Ref. A | p-cyclopentylaminophenylacetic acid |
| 72 | 1-chloro-1-propylcyclopentane Chem. Abst. 52, | p-(1-propylcyclopentylamino)phenylacetic acid |
| 73 | 4-bromo-1,1-dimethylcyclohexane Chem. Abst. 71, 11242c | p-(4,4-dimethylcyclohexylamino)phenylacetic acid |
| 74 | 1-chloro-4-propylcyclohexane Chem. Abst. 68,86671h; 75,128994t | p-(4-propylcyclohexylamino)phenylacetic acid |
| 75 | 2-chloro-1-methylethylcyclohexane Chem. Abst. 70,P87143r; 75,128994t | p-[2(1-methylethyl, cyclohexylamino]phenylacetic acid |
| 76 | 4-(t-butyl)-1-chloro-1-methylcyclohexane Chem. Abst. 68,113898w | p-[4-(t-butyl)-1-methylcyclohexylamino]phenylacetic acid |
| 77 | bromocycloheptane Chem. Abst. 51,9505e; 67.9986s | p-cycloheptylaminophenylacetic acid |
| 78 | bromocyclooctane Chem. Abst. 51,1049e; | p-cycloheptylaminophenylacetic acid |
| 79 | bromocyclononane Chem. Abst. 54,4153f; 69,2306v | p-cyclononylaminophenylacetic acid |
| 80 | bromocyclodecane Chem. Abst. 67,58849h; 69,2306c | p-cyclodecylaminophenylacetic acid |
| 81 | bromocycloundecane | p-cycloundecylaminophenylacetic acid |
| 83 | bromocyclotridecane Chem. Abst. 69,2306c | p-cyclotridecylaminophenylacetic acid |
| 84 | bromocyclotetradecane Chem. Abst. 54,4153f; 54,16141i | p-cyclotetradecylaminophenylacetic acid |
| 85 | bromocyclopentadecane Chem. Abst. 72,P100160g 69,2306c | p-cyclopentadecylaminophenylacetic acid |
| 86 | bromocyclohexadecane Chem. Abst. 69,2306c | p-cyclohexadecylaminophenylacetic acid |
| 87 | 3-bromobicyclopentyl Chem. Abst. 31,7405$^3$; 35,2864 | p-(3-cyclopentyl)cyclopentylamino)phenylacetic acid |
| 88 | (3-bromocyclopentyl)cyclohexane Chem. Abst. 31,7405$^4$ | p-(3-cyclohexylcyclopentylamino)phenylacetic acid |
| 89 | 3-bromo-3'-ethylbicyclopentyl Chem. Abst. 36,48089 | p-[3-(3-ethylcyclopentyl)cyclopentylamino]phenylacetic acid |
| 90 | 2-bromo-1-cyclopentylcyclopentane Chem. Abst. 51,5712f | p-[2-(cyclopentyl)cyclopentylamino]phenylacetic acid |
| 91 | 1-chlorobicyclohexyl Chem. Abst. 30,3807$^1$ | p-[1-(cyclohexyl)cyclohexylamino]phenylacetic acid |
| 92 | 1-chlorobicyclopentyl Chem. Abst. 45,6163b | p-[1-(cyclopentyl)cyclopentylamino]phenylacetic acid |
| 93 | 2-iodomethyldecahydronapthalene Chem. Abst. 41,116b | p-[(2-decahydronaphthyl)methylamino]phenylacetic acid |
| 94 | 2-(2-iodoethyl)decahydronaphthalene Chem. Abst. 41,116b | p-[2-(2-decahydronaphthyl)ethylamino]phenylacetic acid |
| 95 | 1-(4-bromobutyl)decahydronaphthalene Chem. Abst. 45,p175d | p-[4-(1-decahydronaphthyl)butylamino]phenylacetic acid |
| 96 | 1-bromo-1,1-dicyclopentylethane, Chem. Abst. 31,5759$^2$ | p-[(1,1-dicyclopentyl)ethylamino]phenylacetic acid |
| 97 | 1-bromo-4α-methyldecahydronaphthalene Chem. Abst. 53,3265f | p-[1-(4-methyldecahydronaphthyl)amino]phenylacetic acid |
| 98 | 2-(bromomethyl)-1,3,3-trimethylcyclohexane Chem. Abst. 28,2343$^8$ | p-[(1,3,3-trimethylcyclohexyl)methylamino]phenylacetic acid |
| 99 | 6-(3-bromobutyl)-1,5,5-trimethylcyclohexane Chem. Abst. 66,2658q | p-[4-(2,6,6-trimethyl-2-cyclohexenyl)-2-butylamino]phenylacetic acid |
| 100 | 4-(3-chloropropyl)cyclohexane Ref. A | p-[3-(3-cyclohexenyl)propylamino]phenylacetic acid |
| 101 | 3-(4-chlorobutyl)cyclopentene Ref. A | p-[4-(3-cyclopentenyl)butylamino]phenylacetic acid |
| 102 | 1-(4-bromobutyl)cyclohexene Chem. Abst 69,76727n | p-[4-(1-cyclohexenyl)butylamino]phenylacetic acid |
| 103 | 1-(5-bromopentyl)cyclopentene Chem. Abst. 55,27129q | p-[5-(1-cyclopentenyl)pentylamino]phenylacetic acid |
| 104 | 3-(11-chloroundecyl)cyclopentene Chem. Abst. 37,3060f | p-[11-(3-cyclopentenyl)undecylamino]phenylacetic acid |
| 105 | 1-(13-chlorotridecyl)cyclopentene Chem. Abst. 37,5031b | p-[13-(1-cyclopentenyl)tridecylamino]phenylacetic acid |
| 106 | 3-(13-chlorotridecyl)cyclopentene Chem. Abst. 51,7652a | p-[13-(3-cyclopentenyl)tridecylamino]phenylacetic acid |
| 107 | 2-(4-chlorobutyl)decahydronaphthalene Chem. Abst. 70,P87143r | p-[4-(2-decahydronaphthyl)butylamino]phenylacetic acid |
| 108 | 4-bromo-1-(cyclohexyl)cyclohexane Chem. Abst. 69,103618m | p-[4-cyclohexyl)cyclohexylbutylamino]phenylacetic acid |

Ref. A = R. D. Westland, et al., J. Med Chem., 11,1190 (1968)

EXAMPLE 109

Preparation of p-[2-(cyclopentyl)ethylamino]phenylacetic acid

To a solution of cyclopentylethan-2-ol (15.0 g.) and triethylamine (14 ml.) in dry methylene chloride (320 ml.) at −8° C. is added methanesulfonylchloride (5.73 ml.), dropwise. The reaction mixture is stirred at −10° C. for 30 minutes and then diluted with methylene chloride, extracted with ice-water (250 ml.), followed by cold 10% hydrochloric acid (200 ml.); cold saturated sodium bicarbonate (200 ml.) and cold brine (200 ml.). The organic phase is dried over magnesium sulfate and the solvent removed in vacuo to provide crude mesylate.

A solution of 18.1 g. of the above mesylate and 19.8 g. of ethyl p-aminophenylacetate in hexamethylphosphoramide is heated at 120° C. for 20 hours. After cooling, the reaction mixture is diluted with 30 ml. of ethanol:water(1:1) (30 ml.) and chilled. More ethanol is added and the solid material is collected. This solid is recrystallized twice from ethanol to provide the ester.

A mixture of the ester, 22.0 g. of potassium hydroxide and 200 ml. of ethanol-water (8:1) is stirred under reflux for 6 hours. Concentrated hydrochloric acid (about 80 ml.) is added to the warm mixture and cooling and dilution with water affords a white solid which is collected by filtration and recrystallized from ethanol to yield the product as a white solid.

EXAMPLES 110–185

Treatment of the alcohols of Table II below with methanesulfonylchloride to provide the corresponding mesylate followed by treatment with ethyl p-aminophenylacetate followed by saponification and acidification of the resulting substituted p-aminophenylacetate by the procedure of Example 109 produces the indicated p-(substituted amino)phenylacetic acids shown in Table II.

TABLE II

| Example | Starting material | Product |
|---|---|---|
| 110 | 2-isopropyl-5-methylenecyclopentanol Chem. Abst. 66,38074c | p-(2-isopropyl-5-methylene cyclopentylamino)phenylacetic acid |
| 111 | 2-cyclohexen-1-ol Aldrich Chem. Co. | p-(cyclohex-2-enylamino)phenylacetic acid |
| 112 | 4-isopropyl-2-cyclohexen-1-ol Chem. Abst. 69,99290d | p-(4-isopropylcyclohex-2-enylamino)phenylacetic acid |
| 113 | 2-isopropyl-3-cyclohexen-1-ol Chem. Abst. 75,55380m | p-(2-isopropylcyclohex-3-enylamino)phenyl acetic acid |
| 114 | 2-methyl-2-cycloocten-1-olopentane Chem. Abst. 69,27127h | p-(2-(cyclopentyl)cyclopentylamino)phenylacetic acid |
| 115 | 2-cyclononen-1-ol Chem. Abst. 72,30882t | p-(cyclonon-2-enylamino)phenylacetic acid |
| 116 | 3-cyclononen-1-ol Chem. Abst. 75,13957j | p-(cyclonon-3-enylamino)phenylacetic acid |
| 117 | 2-methylenecyclodecanol Chem. Abst. 74,75857w | p-(2-methylenecyclodecylamino)phenylacetic acid |
| 118 | E-3-cyclodecen-1-ol Chem. Abst. 73,87173n | p-(E-cyclodec-3-enylamino)phenylacetic acid |
| 119 | Z-3-cyclodecen-1-ol Chem. Abst. 73,87173n | p-(Z-cyclodec-3-enyl amino)phenylacetic acid |
| 120 | 5-cyclodecen-1-ol Chem. Abst. 71,60514w | p-(cyclodec-5-enylamino)phenylacetic acid |
| 121 | 4-ethyl-2-cyclododecen-1-ol Chem. Abst. 70,114922c | p-(4-ethylcyclododec-2-enylamino)phenylacetic acid |
| 122 | 2-cyclotridecen-1-ol Chem. Abst. 70,114922c | p-(cyclotridec-2-enylamino)phenylacetic acid |
| 123 | 8-cycloheptadecen-1-ol Chem. Abst. 66,2658q | p-(cycloheptadec-8-enylamino)phenylacetic acid |
| 124 | 9-cycloheptadecen-1-ol Chem. Abst. 68,49157z | p-(cycloheptadec-9-enylamino)phenylacetic acid |
| 125 | 2-cyclobutene-1-methanol Chem. Abst. 67,32343p | p-[(cyclobut-2-enyl)methylamino]phenylacetic acid |
| 126 | 1-cyclobutene-1-methanol Chem. Abst. 71,12650r | p-[(cyclobut-1-enyl)ethylamino]phenylacetic acid |
| 127 | 2-cyclopentene-1-methanol Chem. Abst. 71,12650r | p-[(cyclopent-3-enyl)methylamino]phenylacetic acid |
| 128 | 3-cyclopentene-1-methanol Chem. Abst. 73,65783j | p-(4-isopropylcyclohex-2-enylamino)phenylacetic acid |
| 129 | 1-cyclopentene-1-propanol Chem. Abst. 73,66113c | p-[1-(cyclopent-1-enyl)propylamino]phenylacetic acid |
| 130 | 1-cyclohexene-1-methanol Chem. Abst. 70,10773p | p-[(cyclohex-1-enyl)methylamino]phenylacetic acid |
| 131 | 2-cyclohexene-1-ethanol, 30882t Chem. Abst. 69,26424r | p-[(1-cyclohex-2-enyl)ethylamino]phenylacetic acid |
| 132 | 1-(3-cyclohexenyl)-1-propanol Chem. Abst. 67,72634r | p-[(1-cyclohex-3-enyl)propylamino]phenylacetic acid |
| 133 | cis-5-ethyl-3-cyclohexene-1-methanol Chem. Abst. 69,27575c | p-(cis-5-ethylcyclohex-3-enyl)methylaminophenylacetic acid |
| 134 | trans-5-ethyl-3-cyclohexene-1-methanol Chem. Abst. 69,27575c | p-(trans-5-ethylcyclohex-3-enyl)methylaminophenylacetic acid |
| 135 | 1-cycloheptene-1-methanol Chem. Abst. 73,14266k | p-(cyclohept-1-enylmethylamino)phenylacetic acid |
| 136 | 1-cycloheptene-1-ethanol Chem. Abst. 70,37270j | p-[1-(cyclohept-1-enyl)ethylamino]phenylacetic acid |
| 137 | 2-cyclooctene-1-methanol Chem. Abst. 69,36263b | p-(cyclooct-2-enylmethylamino)phenylacetic acid |
| 138 | 4-cyclooctene-1-methanol Chem. Abst. 66,37492a | p-(cyclooct-4-enylmethylamino)phenylacetic acid |
| 139 | 1-cyclooctenylethanol Chem. Abst. 70,37270j | p-(cyclooct-1-enylethylamino)phenylacetic acid |
| 140 | 2-(3-cyclopentenyl)butanol Chem. Abst. 72,133044a | p-[2-ethyl-2-cyclopent-3-enylethylamino]phenylacetic acid |
| 141 | 2,3-dimethyl-2-(2-cyclopentenyl)propanol Chem. Abst. 70,11818u | p-[2-(2,3-dimethylcyclopent-2-enyl)propylamino]phenylacetic acid |
| 142 | 4,6-dimethyl-3-cyclohexen-1-ethanol Chem. Abst. 111623c | p-[2-(4,6-dimethylcyclohex-3-enyl)ethylamino]phenylacetic acid |
| 143 | α-methyl-1-cyclohexene-1-ethanol Chem. Abst. 74,42909v | p-[1-methyl-2-(cyclohex-1-enyl)ethylamino]phenylacetic acid |
| 144 | 4-methyl-3-cyclohexene-1-ethanol Chem. Abst. 75,19601s | p-[2-(4-methylcyclohex-3-enyl)ethylamino]phenyl acetic acid |
| 145 | 1-cyclooctene-1-ethanol Chem. Abst. 70,37270j | p-(2-cyclooct-1-enylethylamino)phenylacetic acid |
| 146 | 1-cyclononene-1-ethanol | p-(2-cyclonon-1-enylethylamino)phenylacetic acid |
| 147 | α,4-dimethyl-3-cyclohexene-1-propanol Chem. Abst. 68,78427t | p-[1-methyl-3-(4-methylcyclohex-3-enyl)propylamino]phenylacetic acid |
| 148 | 1-cyclohexene-1-propanol Chem. Abst. 70,87111d | p-(3-cyclohex-1-enylpropylamino)phenylacetic acid |
| 149 | 3-cyclohexene-1-propanol Chem. | p-(3-cyclohex-3-enylpropylamino)phenylacetic |

TABLE II-continued

| Example | Starting material | Product |
|---|---|---|
| 150 | 3-cyclohexene-1-butanol Chem. Abst. 69,43158z Abst. 69,49158z | acid p-(4-cyclohex-3-enyl-butylamino)phenylacetic acid |
| 151 | α,α-dimethyl-2-cyclopentene-1-undecanol Chem. Abst. 72,110860z | p-[(1,1-dimethyl-11-cyclopent-2-enyl)undecylamino]phenylacetic acid |
| 152 | 4-isopropylidene-2,2-dimethylcyclobutanol Chem. Abst. 73,24996n | p-(2,2-dimethyl-4-isopropylidenecylobutyl-amino)phenylacetic acid |
| 153 | 2-cyclopenten-1-ol Chem. Abst. 68,39177s | p-(cyclopent-2-enylamino)-phenylacetic acid |
| 154 | 3-cyclopenten-1-ol Chem. Abst. 66,11504r | p-(cyclopent-3-enylamino)-phenylacetic acid |
| 155 | 3-cyclohexen-1-ol Chem. Abst. 69,26837c | p-(cyclohex-3-enylamino)-phenylacetic acid |
| 156 | 2,2-dimethyl-6-methylenecyclohexanol | p-(2,2-dimethyl-6-enyl-cyclohexylamino)phenyl-acetic acid |
| 157 | 2-methylenecycloheptanol Chem. Abst. 69,27127h | p-(2-methylenecycloheptylamino)phenylacetic acid |
| 158 | 2-methyl-2-cyclohepten-1-ol Chem. Abst. 69,27127h | p-(2-methylcyclohept-2-enylamino)phenylacetic acid |
| 159 | 2-methyl-6-methylenecycloheptanol Chem. Abst. 67,11600e | p-(2-methyl-6-methylenylcycloheptylamino)-phenylacetic acid |
| 160 | 3,7-dimethyl-3-cyclohepten-1-ol Chem. Abst. 67,11600e | p-(3,7-dimethylcyclohept-3-enylamino)phenylacetic acid |
| 161 | 4-cycloocten-1-ol Chem. Abst. 70,28287t | p-(cycloot-4-enylamino) phenylacetic acid |
| 162 | 3-cycloocten-1-ol Chem. Abst. 66,104593z | p-(cyclooct-3-enylamino)-phenylacetic acid |
| 163 | 2-cycloocten-1-ol Chem. Abst. 68,39177s | p-(cyclooct-2-enylamino)-phenylacetic acid |
| 164 | 4-methylenecyclooctanol Chem. Abst. 70,28445t | p-(4-methylenecyclooctyl-amino)phenylacetic acid |
| 165 | α-methyl-5-methylene-cycloooctanemethanol Chem. Abst. 68,104595t | p-[1-(5-methylenecyclo-octylethylamino]phenyl-acetic acid |
| 166 | 5-methylenecyclooctanemethanol Chem. Abst. 66,37492a | p-[5-methylenecyclooctyl-methylamino]phenylacetic acid |
| 167 | 1 3-dimethyl-2-methylenecyclopentane-methanol Chem. Abst. 73,24996n | p-[(1,3-dimethyl-2-methyl-enecyclopentyl)methyl-aminophenylacetic acid |
| 168 | E-4-cyclopropyl-3-buten-2-ol | p-[E-2-(4-cyclopropyl) but-3-enylamino]phenyl-acetic acid |
| 169 | Z-4-cyclopropyl-3-buten-2-ol Chem. Abst. 70,3413t | p-[Z-2-(4-cyclopropyl)-but-3-enylamino]phenyl-acetic acid |
| 170 | α-methylenecyclohexaneethanol Chem. Abst. 66,45950p | p-[(1-methylene-2-cyclohexyl)ethyl-amino]phenylacetic acid |
| 171 | β-methylenecyclohexaneethanol Chem. Abst. 75,139951c | p-[(2-methylene-2-cyclohexyl)ethylamino] phenylacetic acid |
| 172 | E-2-(3,3-dimethylcyclohexylidenyl)ethanol Chem. Abst. 75,110431x | p-[E-2-(3,3-dimethylcyclohexylidenyl)ethyl]amino phenylacetic acid |
| 173 | Z-2-(3,3-dimethylcyclohexylidenyl)ethanol Chem. Abst. 75,110431x | p-[Z-2-(3,3-dimethylcyclohexylidenylethylamino]-phenylacetic acid |
| 174 | E-4-cyclopentyl-2-buten-1-ol Chem. Abst. 75,48349w | p-(4-cyclopentylbut-2-enylamino)phenylacetic acid |
| 175 | E-4-cyclohexyl-2-buten-1-ol Chem. Abst. 75,48349w | p-[E-4-cyclohexylbut-2-en-ylamino]phenylacetic acid |
| 176 | 2-vinylcyclopentane-ethanol Chem. Abst. 66,104477q | p-[2-(2-vinylcyclopentyl)-ethylamino]phenylacetic acid |
| 177 | 3-isopropyl-1-methyl-cyclopentanemethanol Chem. Abst. 66,38061w | p-[(3-isopropyl-2-methyl-cyclopentyl)methylamino]-phenylacetic acid |
| 178 | 1-allyl-2-methylcyclo-hexanol Chem. Abst. 71,29919h | p-(1-allyl-2-methylcyclo-hexylamino)phenylacetic acid |
| 179 | 2-isopropenylcyclo-hexanol Chem. Abst. 72,12663t | p-(2-isopropenylcyclo-hexylamino)phenylacetic acid |
| 180 | 1-(isopropenylcyclo-hexanol Chem. Abst. 75,139951c | p-(1-isopropenylcyclo-hexylamino)phenylacetic acid |
| 181 | 2-allylcyclohexanol Chem. Abst. 70,96517t | p-(2-allylcyclohexyl-amino)phenylacetic acid |
| 182 | 3-allylcyclohexanol Chem. Abst. 69,86453j | p-(3-allylcyclohexyl-amino)phenylacetic acid |
| 183 | 1-allylcyclohexanol Chem. Abst. 66,374866 | p-(1-allylcyclohexyl-amino)phenylacetic acid |
| 184 | 1-(3-butenyl)-2-methyl cycloheptanol Chem. Abst. 69,106892q | p-[1-(3-butenyl)-2-methyl-cycloheptylamino] phenylacetic acid |
| 185 | 1-allylcyclododecanol Chem. Abst. 68,95381r | p-(1-allylcyclododecyl-amino)phenylacetic acid |
| 186 | 2-butyl-2-cyclopenten-1-ol Chem. Abst. 71,38404p | p-(2-butycyclopent-2-en-ylamino)phenylacetic acid |

EXAMPLE 187

Preparation of Esters

Treatment of the acids of Examples 1–186 with trifluoroacetic anhydride to provide the N—$COCF_3$ derivatives, followed by treatment with thionyl chloride to provide the N—$COCF_3$ acid chloride, followed by treatment with one of the following alcohols, followed by removal of the N—$COCF_3$ group with sodium hydroxide, provides the corresponding esters of the starting acid.

Alcohols: methanol, ethanol, 2-methoxyethanol, butanol, pentanol, hexanol, cyclopentanol, cyclohexanol, 1,2-propanediol, 1,3-propanediol, ethylene glycol, glycerol, glycidol, glycolic acid, citric acid, tartaric acid, malid acid, methyl glycolate, 2-hydroxypropionic acid, 3-hydroxybutyhric acid 4-hydroxybutyric acid, glyceric acid, 3-diethylamino-1-propanol, 1-diethylamino-2-propanol, 1-dimethylamino-2-propanol, 3-dimethylamino-1-propanol, 2-diisopropylaminoethanol, 3-diethylamino-1,2-propanediol, N-piperidineethanol, N,N-diethylethanolamine, benzyl alcohol, p-fluorobenzyl alcohol, p-bromobenzyl alcohol, p-chlorobenzyl alcohol, p-methoxylbenzyl alcohol, m-chlorobenzyl alcohol, m-(trifluoromethyl)benzyl alcohol, p-carboxybenzyl alcohol, phenol p-fluorophenol, p-bromophenol, p-chlorophenol, p-methoxyphenol, p-carboxyphenol, m-(trifluoromethyl)phenol, 4-cyanophenol, 3-hydroxypyridine, 2-chloro-3-hydroxypyridine, and 5-carboxy-3-hydroxypyridine.

EXAMPLE 188

Preparation of 4-[(cyclohexyl)methylamino]hydrocinnamic acid

A 4 g. sample of ethyl 4-[(cyclohexyl)methylamino]hydrocinnamate is hydrolyzed with 1.6 g. 85% potassium hydroxide in 60 ml. 95% ethanol by refluxing the solution for 5 hours. The solution is cooled, diluted with 100 ml. water and acidified to pH 4.5 with 37% hydrochloric acid. The precipitate is collected, dried in vacuo and crystallized from acetone to yield the title compound as white powder.

EXAMPLE 189

Preparation of 1-methanesulfonyloxy-2-allylcyclohexane

To a mixture of 250 ml. of dichloromethane, 25 g. 2-allylcyclohexanol and 16.7 g. of triethylamine cooled in an ice-salt bath to −10° C. is added dropwise, over 15 minutes, 18.9 g. of methanesulfonyl chloride. The mixture is cooled at −10° C. to −15° C. for 30 minutes and then washed with 300 ml. each of cold water, 10% hydrochloric acid, sodium carbonate solution and with saturated sodium chloride solution. The organic layer is dried with magnesium sulfate and concentrated in vacuo to give a pale yellow oil.

EXAMPLE 190

Preparation of ethyl 4-[(2-methylcyclopentyl)methylamino]phenylacetate

To a cold (−20°) stirred solution of 10.8 g. 1-hydroxymethyl-2-methylcyclopentane prepared by lithium aluminum hydride reduction of methyl 2-methylcyclopentanecarboxylate and 13.4 ml. triethylamine in 300 ml. ether is added dropwise 5.6 ml. methanesulfonyl chloride in 5 ml. of either. After addition is completed, the solution is warmed to room temperature, stirred for 30 minutes and filtered directly into a solution of 23.1 g. ethyl 4-aminophenyl acetate in 100 ml. ether. After 17 hours at room temperature, the precipitate is filtered and washed with several portions of methylene chloride. The organic solution is washed twice with 100 ml. water, 100 ml. brine, dried and evaporated. The tan residue is crystallized from ethanol and from acetonitrile to yield the title compound as white crystals.

EXAMPLE 191

Preparation of ethyl 4-[(3-isopropyl-2-methylcyclopentyl)methylamino]hydrocinnamate A solution of 8.6 ethyl 4-aminohydrocinnamate, 9.77 g. 3-isopropyl-2-methylcyclopentanecarboxaldehyde and a few crystals of 2,4-dinitrobenzenesulfonic acid in 250 ml. toluene is refluxed under a Dean-Stark trap for 17 hours, whereupon the theoretical amount (0.8 ml.) water has been collected. The toluene is evaporated to yield ethyl 3-[4-(3-isopropyl-2-methylcyclopentyl)methyleneamino)phenyl]propionate as a crystalline mass.

To a mixture of 17.8 g. of the above compound in 250 ml. ethanol is added 1.68 g. sodium borohydride and the mixture is stirred at room temperature for 18 hours. Excess reagent is decomposed by addition of 10 ml. acetic acid. The solution is concentrated in vacuo and the residue is partitioned between toluene and aqueous potassium carbonate. After drying, the toluene is evaporated to yield a solid. Crystallization from acetonitrile and from ethanol affords the title compound as white crystals.

EXAMPLE 192

Preparation of ethyl 3-[4-(2-allylcyclohexylamino)phenyl]propionate

A mixture of 5.0 g. of ethyl 4-aminohydrocinnamate, 10.0 g. of 1-methanesulfonyloxy-2-allylcyclohexane (prepared by the method of Example 189), 4.2 g. of anhydrous powdered potassium carbonate and 40 ml. hexamethylphosphoramide is heated to 80 for 17 hours. The mixture is then cooled, diluted with water and extracted with ethyl ether. The ether extracts are washed with water, dried and evaporated. The residue is recrystallized from ethanol yielding the title compound as white crystals.

EXAMPLE 193

Preparation of ethyl 4-[(4-cycloheptyl)butylamino]cinnamate

A mixture of ethyl p-aminocinnamate, 5.9 g. 4-bromobutylcycloheptane and one equivalent of anhydrous powdered potassium carbonate in 50 ml. hexamethylphosphoramide is heated for 20 hours at 60° C. The mixture is then cooled, diluted with water and extracted with ether. The combined ether extracts are dried, filtered and evaporated. Crystallization from acetonitrile provides the title compound as white crystals.

TABLE III

The following 4-[(cycloalkyl or cycloalkenyl substituted)amino, alkylamino or alkenylamino]hydrocinnamates are prepared from the appropriate starting material by the method shown. Alcohols are converted to the corresponding mesylate by the method of Example 189.

| Example No. | Method of Example | 4-(Substituted-amino)hydrocinnamte |
|---|---|---|
| 194 | 190 | Ethyl 4-[(cyclopentyl)methylamino]hydrocinnamate |
| 195 | 193 | Ethyl 4-[1-(1,4-dimethylcyclohexyl)-2-propylamino]hydrocinnamate |
| 196 | 191 | Ethyl 4-(2-cyclopentylbutylamino)hydrocinnamate |
| 197 | 192 | Ethyl 4-(4-cyclopentylbutylamino)hydrocinnamate |
| 198 | 193 | Ethyl 4-cyclodecylaminohydrocinnamate |
| 199 | 190 | Ethyl 4-(3-cyclohexylcyclopentylamino)hydrocinnamate |
| 200 | 192 | Ethyl 4-[2-(2-decahydronaphthyl)ethylamino]hydrocinnamate |
| 201 | 190 | Ethyl 4-(2-isopropyl-5-methylenecyclopentylamino)hydrocinnamate |
| 202 | 193 | Ethyl 4-(4-isopropylcyclohex-2-enylamino)hydrocinnamate |
| 203 | 190 | Ethyl 4-[2-(2,3-dimethylcyclopent-2-enyl)propylamino]hydrocinnamate |
| 204 | 192 | Ethyl 4-(cyclopent-2-enylamino)hydrocinnamate |
| 205 | 192 | Ethyl 4-(1-allylcyclododecylamino)hydrocinnamate |

TABLE IV

The following 4-[(cycloalkyl or cycloalkenyl substituted)amino, alkylamino or alkenylamino]hydrocinnamic acids are prepared from the esters of Table III by the method of Example 188.

| Example No. | 4-(Substituted-amino)hydrocinnamic acids |
|---|---|
| 206 | 4-[(Cyclopentyl)methylamino]hydrocinnamic acid |
| 207 | 4-[1-(1,4-Dimethylcyclohexy)-2-propylamino]hydrocinnamic acid |
| 208 | 4-(2-Cyclopentylbutylamino)hydrocinnamic acid |
| 209 | 4-(4-Cyclopentylbutylamino)hydrocinnamic acid |
| 210 | 4-Cyclodecylaminohydrocinnamic acid |
| 211 | 4-(3-Cyclohexylcyclopentylamino)hydrocinnamic acid |
| 212 | 4-[2-(2-Decahydronaphthyl)ethylamino]hydrocinnamic acid |
| 213 | 4-(2-Isopropyl-5-methylenecyclopentylamino)hydrocinnamic acid |
| 214 | 4-(4-Isopropylcyclohex-2-enylamino)hydrocinnamic acid |
| 215 | 4-[2-(2,3-Dimethylcyclopent-2-enyl)propylamino]hydrocinnamic acid |
| 216 | 4-(Cyclopent-2-enylamino)hydrocinnamic acid |

TABLE IV-continued

The following 4-[(cycloalkyl or cycloalkenyl substituted)amino, alkylamino or alkenylamino]hydrocinnamic acids are prepared from the esters of Table III by the method of Example 188.

| Example No. | 4-(Substituted-amino)hydrocinnamic acids |
|---|---|
| 217 | 4-(1-Allylcyclododecylamino)hydrocinnamic acid |

TABLE V

The following 4-[(cycloalkyl or cycloalkenyl substituted)amino, alkylamino or alkenylamino]cinnamates are prepared from the appropriate starting materials by the methods shown. Alcohols are converted to their corresponding mesylate by the method of Example 189.

| Example No. | Method of Example | 4-(Substituted-amino)cinnamate |
|---|---|---|
| 218 | 190 | Ethyl 4-[(cyclopentyl)methylamino]-cinnamate |
| 219 | 193 | Ethyl 4-[(4-methylcyclohexyl)methylamino]cinnamate |
| 220 | 192 | Ethyl 4-[1-(1,4-dimethylcyclohexyl)-2-propylamino]cinnamate |
| 221 | 192 | Ethyl 4-[2-(2-methylcyclohexyl)ethylamino]cinnamate |
| 222 | 193 | Ethyl 4-[3-(3-ethylcyclohexyl)-2-methyl]propylaminocinnamate |
| 223 | 192 | Ethyl 4-[5-(cyclopropyl)-2-pentylamino]cinnamate |
| 224 | 191 | Ethyl 4-(3-cyclohexylcyclopentylamino)cinnamate |
| 225 | 190 | Ethyl 4-[4-(1-decahydronaphthyl)butylamino]cinnamate |
| 226 | 193 | Ethyl 4-(cyclonon-2-enylamino)cinnamate |
| 227 | 190 | Ethyl 4-[(1-cyclohex-2-enyl)ethylamino]cinnamate |
| 228 | 192 | Ethyl 4-[1-methyl-2-(cyclohex-1-enyl)ethylamino]cinnamate |
| 229 | 193 | Ethyl 4-[(2-methylene-2-cyclohexylethyl)amino]cinnamate |
| 230 | 192 | Ethyl 4-(1-isopropenylcyclohexylamino)cinnamate |

TABLE VI

The following 4-[cycloalkyl or cycloalkenyl substituted)amino, alkylamino or alkenylamino]cinnamic acids are prepared from the esters of Table V by the method of Example 188.

| Example No. | 4-(Substituted-amino)cinnamic acid |
|---|---|
| 231 | 4-[(Cyclopentyl)methylamino]cinnamic acid |
| 232 | 4-[(4-Methylcyclohexyl)methylamino]cinnamic acid |
| 233 | 4-[1-(1,4-Dimethylcyclohexyl)-2-propylamino]cinnamic acid |
| 234 | 4-[2-(2-Methylcyclohexyl)ethylamino]cinnamic acid |
| 235 | 4-[3-(3-Ethylcyclohexyl)-2-methylpropylamino]cinnamic acid |
| 236 | 4-[5-(Cyclopropyl)-2-pentylamino]cinnamic acid |
| 237 | 4-(3-Cyclohexylcyclopentylamino)cinnamic acid |
| 238 | 4-[4-(1-Decahydronaphthyl)butylamino]cinnamic acid |
| 239 | 4-(Cyclonon-2-enylamino)cinnamic acid |
| 240 | 4-[(1-Cyclohex-2-enyl)ethylamino]cinnamic acid |
| 241 | 4-[1-Methyl-2-(cyclohex-1-enyl)ethylamino]cinnamic acid |
| 242 | 4-[(2-Methylene-2-cyclohexylethyl)amino]cinnamic acid |
| 243 | 4-(1-Isopropenylcyclohexylamino)cinnamic acid |

TABLE VII

The following 4-[(cycloalkyl or cycloalkenyl substituted)amino, alkylamino or alkenylamino]phenyl-propiolates are prepared from the appropriate starting materials by the methods shown. Alcohols are converted to their corresponding mesylate by the method of Example 189.

| Example No. | Method of Example | 4-(Substituted-amino)phenylpropiolate esters |
|---|---|---|
| 244 | 191 | Ethyl 4-[(cyclopentyl)methylamino]-phenylpropiolate |
| 245 | 193 | Ethyl 4-(2-cyclopentylbutylamino)-phenylpropiolate |
| 246 | 193 | Ethyl 4-(4-cyclopentyl)-butylamino-phenylpropiolate |
| 247 | 192 | Ethyl 4-[2-(2-decahydronaphthyl)ethylamino]phenylpropiolate |
| 248 | 192 | Ethyl 4-(4-isopropylcyclohex-2-enyl-amino)phenylpropiolate |
| 249 | 190 | Ethyl 4-(cyclopent-2-enylamino)phenyl-propiolate |
| 250 | 190 | Ethyl 4-(1-allylcyclododecylamino)-phenylpropiolate |

TABLE VIII

The following 4-[cycloalkyl or cycloalkenyl substituted)amino, alkylamino, or alkenylamino]phenyl-propiolic acids are prepared from the esters of Table VII by the method of Example 188.

| Example No. | 4-(Substituted-amino)phenylpropiolic acid |
|---|---|
| 251 | 4-[(Cyclopentyl)methylamino]phenylpropiolic acid |
| 252 | 4-(2-Cyclopentylbutylamino)phenylpropiolic acid |
| 253 | 4-(4-Cyclopentylbutylamino)phenylpropiolic acid |
| 254 | 4-[2-(2-Decahydronaphthyl)ethylamino]phenyl-propiolic acid |
| 255 | 4-(4-Isopropylcyclohex-2-enylamino)phenyl-propiolic acid |
| 256 | 4-(Cyclopent-2-enylamino)phenylpropiolic acid |
| 257 | 4-(1-Allylcyclododecylamino)phenylpropiolic acid |

TABLE IX

The following 4-[(cycloalkyl or cycloalkenyl substituted)amino, alkylamino or alkenylamino]phenylbutyrates are prepared from the appropriate mesylates by the method of Example 192. The requisite mesylates are prepared by the method of Example 189

| Example No. | 4-(Substituted-amino)phenylbutyrate esters |
|---|---|
| 258 | Ethyl 4-[4-(2-butylcyclopent-2-enylamino)-phenyl]butyrate |
| 259 | Ethyl 4-[4-(1-allylcyclohexylamino)phenyl]-butyrate |
| 260 | Ethyl 4-[4-(cyclooct-2-enylamino)phenyl]-butyrate |
| 261 | Ethyl 4-[4-(cycloheptyl)butylamino]phenyl-butyrate |
| 262 | Ethyl 4-[4-(1-cyclopentylethylamino)phenyl]-butyrate |
| 263 | Ethyl 4-[4-(cyclooctylmethylamino)phenyl]-butyrate |

TABLE X

The following 4-[cycloalkyl or cycloalkenyl substituted amino, alkylamino or alkenylamino]phenylbutyric acids are prepared from the esters of Table IX by the method of Example 188.

| Example No. | 4-(Substituted-amino)phenylbutyric acid |
|---|---|
| 264 | 4-[4-(2-Butylcyclopent-2-enylamino)phenyl]-butyric acid |
| 265 | 4-[4-(1-Allylcyclohexylamino)phenyl]butyric acid |
| 266 | 4-[4-(Cyclooct-2-enylamino)phenyl]butyric acid |
| 267 | 4-[4-(Cycloheptyl)butylamino]phenylbutyric acid |

TABLE X-continued

The following 4-[cycloalkyl or cycloalkenyl substituted amino, alkylamino or alkenylamino]phenylbutyric acids are prepared from the esters of Table IX by the method of Example 188.

| Example No. | 4-(Substituted-amino)phenylbutyric acid |
| --- | --- |
| 268 | 4-[4-(1-Cyclopentylethylamino)phenyl]butyric acid |
| 269 | 4-[4-(Cyclooctylmethylamino)phenyl]butyric acid |

EXAMPLE 270

Preparation of 4-(2-allylcyclohexylamino)acetophenone p-Aminoacetophenone is heated with 5 g. 1-methanesulfonyloxy-2-allylcyclohexane (prepared by the method of Example 189) in 50 ml. hexamethylphosphoramide containing anhydrous potassium carbonate (1.9 g.) for 16 hours a 100° C. The solution is cooled to room temperature, filtered to remove solids, and the filtrate is diluted with cold water (50 ml.). The amber solid so obtained is collected and and washed with water. Recrystallization from ethanol followed by dichloromethane provides 4-(2-allylcyclohexylamino)acetophenone.

TABLE XI

The following 4-[(cycloalkyl or cycloalkenyl substituted)amino, alkylamino or alkenylamino]acetophenones are prepared by the method of Example 270. The requisiste mesylates are prepared by the method of Example 189.

| Example No. | 4-(Substituted-amino)acetophenone |
| --- | --- |
| 271 | 4-(2-Butylcyclopent-2-enylamino)acetophenone |
| 272 | 4-[(1-Cyclohex-2-enyl)ethylamino]acetophenone |
| 273 | 4-(Cycloheptadec-8-enylamino)acetophenone |
| 274 | 4-(2-Cyclohexylethylamino)acetophenone |
| 275 | 4-[(Cyclopentyl)methylamino]acetophenone |

EXAMPLE 276

Preparation of sodium 4-(1-cyclopentylethylamino)phenylacetate

A mixture of 3.62 g. of 4-(1-cyclopentylethylamino)-phenylacetic acid and 25 ml. of ethanol water (9:1) containing 0.400 g. of sodium hydroxide is stirred for 4 hours. The mixture is filtered and the residue washed with 10 ml. of ethanol-water (9:1) and dried in vacuo for 24 hours to yield 4-(1-cyclopentylethylamino)phenyl acetate as a white solid.

EXAMPLE 277

Preparation of 4-(2-cyclopentylbutylamino)phenylacetyl chloride

A cold solution of 25 g. 4-(2-cyclopentylbutylamino)-phenylacetic acid in 500 ml. dimethoxyethanemethylene chloride (4:1) is prepared and dry hydrochloric acid is bubbled through the solution until no more precipitate forms. The solution is treated with 25 ml. thionyl chloride and refluxed until all of the precipitate has dissolved. The solvents are evaporated to yield the acid chloride hydrochloride as an orange, semi-crystalline mass.

EXAMPLE 278

Preparation of 4-(N-trifluoroacetyl-1-cyclopentylethylamino)phenylacetyl chloride A stirred ice-cold suspension of 9 g. 4-(1-cyclopentylethylamino)phenylacetic acid in 100 ml. of dimethoxyethane and 16 l. of pyridine is treated with 18 ml. of trifluoroacetic anhydride at 0° C. The solution is stirred for 30 minutes at room temperature and then diluted with 300 ml. ether and 100 g. ice. After stirring vigorously for 15 minutes, the phases are separated, the ehter solution is washed with brine, dried and evaporated to a white, amorphous solid.

To a solution of 9.2 g. of the above solid in 30 ml. methylene chloride and 0.5 ml. dimethylformamide is added 5.7 ml. thionyl chloride. After 20 hours at reflux, the solvents are evaporated to yield 4-[N-trifluoroacetyl-1-cyclopentylethylamino)phenylacetyl chloride as a light yellow, mobile oil.

EXAMPLE 279

Preparation of 4-(N-carbobenzyloxy-N-cyclooctylmethylamino)-phenylacetyl chloride To 15 g. 4-(cyclooctylmethylamino)phenylacetic acid in 200 ml. warm chloroform is added a solution of 12 g. sodium carbonate in 150 ml. water. To the vigorously stirred solution is added 10 g. carbobenzyloxy chloride. After 2 hours stirring at 40° C., the layers are separated, washed three times with 1 N hydrochloric acid, dried, and evaorated to an oil. The oil is dissolved in 30 ml. Prevaporated to an oil. The oil is dissolved in 300 ml. toluene, treated with 15 ml. thionyl chloride and the solution is refluxed for 5 hours. The solvents are evaporated and the residue is dissolved three times in toluene, evaporating each time ultimately to yield 4-(N-carbobenzyloxycyclooctylmethylamino)phenylacetyl chloride as a viscous, orange oil.

EXAMPLE 280

Preparation of 1-[4-(N-tert-butyloxycarbonyl)cyclopentylethylamino-phenylacetyl]imidazole To a solution of 10 g. 4-(cyclopentylethylamino)-phenylacetic acid in 100 ml. dioxane is treated with 4.0 g. tert-butylazidoformate and 10 ml. pyridine. After stirring at room temperature for 18 hours, the protected amidoacid is precipitated from solution by the addition of 150 ml. water. The solid is collected, thoroughly dried, and dissolved in 200 ml. of a mixture consisting of methylene chloride/dimethoxyethane/pyridine (1:4:1). To this solution is stirred overnight at room temperature and the solvents are evaporated to yield 1-[4-N-tert-butyloxycarbonyl)cyclopentylethylamino-phenylacetyl]imidazole as an orange oil.

EXAMPLE 281

Preparation of diethyl 4-(1-cyclopentylethylamino)benzoylmalonate

A solution of 26.6 g. of diethyl malonate and 10 ml. of 1,2-dimethoxyethane is added to a suspension of 4.0 g. of 4-(1-cyclopentylethylamino)benzoyl chloride hydrochloride in 1,2-dimethoxyethane under argon. A solution of 17.3 g. of 1,2-dimethoxyethane is then added. The reaction mixture is refluxed for 4.5 hours, cooled, poured on ice, acidified, and extracted with ether. The ether solution is washed with water and saturated sodium chloride solution, dried over anhydrous sodium sulfate and concentrated to dryness. Addition of a small amount of ethanol to the residue gives a solid which is filtered and discarded. The ethanol filtrate is concentrated and the residue is recrystallized from ether to yield diethyl 4-(1-cyclopentylethylamino)benzoylmalonate.

EXAMPLE 282

Preparation of tert-butyl ethyl 4-(1-cyclopentylethylamino)benzoylmalonate

A solution of 28.0 g. of tert-butyl ethyl malonate in 10 ml. of 1,2-dimethoxyethane is added to a suspension of 4.0 g. of sodium hydride in 1,2-dimethoxyethane under argon. A solution of 17.3 g. of 4-(1-cyclopentylethylamino)benzoyl chloride hydrochloride in 1.2-dimethoxyethane is then added. The reaction mixture is refluxed for 5 hours, cooled, poured on ice and extracted with ether. The ether solution is washed with water and saturated sodium chloride solution, dried over anhydrous sodium sulfate and concentrated to dryness. The residue is then recrystallized from ether to yield tert-butyl ethyl 4-(1-cyclopentylethylamino)benzoyl malonate.

EXAMPLE 283

Preparation of ethyl 2-[4-(1-cyclopentylethylamino)benzoyl]acetoacetate

A solution of 21.6 g. of ethyl acetoacetate and 10 ml. of 1,2-dimethoxyethane is added to a suspension of 4.0 g. of sodium hydride in 1,2-dimethoxyethane under argon. A solution of 17.3 g. of 4-(1-cyclopentylethylamino)benzoyl chloride hydrochloride in 1,2-dimethoxyethane is then added. The reaction mixture is refluxed for 5 hours, cooled, poured on ice and extracted with ether. The ether solution is washed with water and saturated sodium chloride solution, dried over anhydrous sodium sulfate and concentrated to dryness. Recrystallization from ether affords ethyl 2-[4-(1-cyclopentylethylamino)benzoyl]acetoacetate as a white solid.

EXAMPLE 284

Preparation of ethyl 4-(1-cyclopentylethylamino)benzoylacetate

A solution of 3.0 g. of tert-butyl ethyl 4-(1-cyclopentylethylamino)benzoylmalonate 10 ml. of trifluoroacetic acid is warmed with stirring for 3 hours. The solution is poured onto ice and neutralized with potassium hydroxide. The resulting precipitate is collected by filtration, washed with water and dried. Recrystallization from chloroform affords ethyl 4-(1-cyclopentylethylamino)benzoylacetate.

EXAMPLE 285

Preparation of 4-(1-cyclopentylethylamino)benzoyl acetic acid

Two grams of ethyl 4-(1-cyclopentylethylamino)benzoylacetate is added to a solution of potassium hydroxide in 50 ml. of 1:9 water-ethanol. The reaction of neutralization with sulfuric acid gave a precipitate which is filtered, washed with water, and dried to yield 4-(1-cyclopentylethylamino)benzoylacetic acid.

EXAMPLE 286

Preparation of 4'-(1-cyclopentylethylamino)-2-(methylsulfinyl)acetophenone

To a solution of 5.8 g. of dimethyl sulfoxide, dried over sieves, and 50 ml. of tetrahydrofuran is slowly added 28 ml. of n-butyllithium (2.4 M in hexane). To this mixture is added 10 g. of methyl 4-(1-cyclopentylethylamino)benzoate in 200 ml. of tetrahydrofuran. After two hours, the reaction mixture is poured onto ice, acidified with dilute hydrochloric acid and quickly extracted with chloroform. The chloroform extract is washed with water and saturated sodium chloride solution, and dried over anhydrous sodium sulfate. Concentration affords a solid which is washed with 500 ml. of hot hexane, filtered while hot and then washed with hexane. The white solid is dried in vacuo to yield 4'-(1-cyclopentylethylamino)-2-(methylsulfinyl)acetophenone.

EXAMPLE 287

Preparation of 4'-(1-cyclopentylethylamino)-2-(phenylsulfonyl)acetophenone

A solution of 864 mg. of sodium hydride and 5.3 g. of methylphenylsulfone in 20 ml. of 1,2-dimethoxyethane is stirred at 6° C. for one hour under an atmosphere of argon. To this solution is added a solution of 5.0 g. of methyl (1-cyclopentylethylamino)benzoate in 50 ml. of tetrahydrofuran and the reaction mixture is stirred at 60° C. for 1.5 hours. The mixture is cooled, poured onto ice, acidified with dilute hydrochloric acid and pH 3 and then extracted with chloroform. The organic layer is separated, washed with water and saturated sodium chloride solution, dried over anhydrous sodium sulfate and then concentrated to dryness. The crude solid is chromatographed on silica gel, eluting with methylene chloride to yield 4'-(1-cyclopentylethylamino)-2-(phenylsulfonyl)acetophenone.

EXAMPLE 288

Preparation of 4'-(1-cyclopentylethylamino)-2-(phenylsulfinyl)acetophenone

To a solution of 6.2 g. of methylphenylsulfoxide, dried over sieves, and 50 ml. of tetrahydrofuran is slowly added 28 ml. of n-butyllithium (2.4 M in hexane). To this mixture is added 10 g. of a solution of methyl 4-(1-cyclopentylethylamino)benzoate in 200 ml. of tetrahydrofuran. After two hours, the reaction mixture is poured into ice, acidified with diluted hydrochloric acid and quickly extracted with chloroform. The chloroform layer is washed with water and saturated sodium chloride solution and dried over anhydrous sodium sulfate. Concentration affords a solid which is washed with 500 ml. of hot hexane, filtered while hot, and then washed with 50 ml. of hexane. The white solid is dried in vacuo yielding 4'-(1-cyclopentylethylamino)-2-(phenylsulfinyl)acetophenone.

EXAMPLE 289

Preparation of 3-[4'-(1-cyclopentylethylamino)benzoyl]-2,4-pentanedione

A solution of 28.4 g. of 2,4-pentanedione and 20 ml. of 1,2-dimethoxyethane is added to a suspension of 13.6 g. of sodium hydride in 220 ml. of 1,2-dimethoxyethane under argon. A solution of 28.7 g. of 4-(1-cyclopentylethylamino)benzoyl chloride hydrochloride in 1,2-dimethoxyethane is then added. The reaction mixture is stirred at room temperature for 12 hours, cooled, poured on ice and extracted with ether. The ether solution is washed with water and saturated sodium chloride solution, dried over anhydrous sodium sulfate and concentrated. The residue is then chromatographed over silica gel to yield 3-[4'-(1-cyclopentylethylamino)-benzoyl]-2,4-pentanedione.

EXAMPLE 290

Preparation of methyl 3-[4-(1-cyclopentylethylamino)benzoyl]propionate

A mixture of 35 g. of 3-(4-acetamidobenzoyl)propionic acid, 700 ml. of methanol and 1.4 ml. of concentrated sulfuric acid is refluxed for 76 hours. The solution is cooled to 35° C. and poured onto 7 g. of anhydrous sodium acetate while stirring. The reaction mixture is stirred in an ice-bath. The solid is collected and washed with cold methanol to yield 3-(4-aminobenzoyl)propionate as a white solid. A mixture of this solid, 9.2 g. of 1-cyclopentylethylbromide and 4.2 g. of potassium carbonate is stirred for 20 hours at 125° C. under nitrogen. The mixture is then cooled to 25° C. and 30 ml. of water is added. After stirring, the product is filtered and washed with water. Recrystallization from methanol affords methyl 3-[4-(1-cyclopentylethylamino)benzoyl]propionate as a white solid.

EXAMPLE 291

Preparation of 3-[4-(1-cyclopentylethylamino)benzoyl]propionic acid

A solution of 5.4 g. of methyl 3-[4-(1-cyclopentylethylamino)benzoylpropionate is stirred with 5.4 g. of potassium hydroxide in 100 ml. of 95% ethanol for 3 hours at reflux. The reaction mixture is cooled, diluted with 50 ml. cf ethanol and 100 ml. of water, neutralized with hydrochloric acid. The solution is cooled to room temperature and filtered. The white solid is washed with 50% aqueous ethanol and dried. The product is recrystallized from ethanol to yield 3-[4-(1-cyclopentylethylamino)benzoyl]propionic acid.

TABLE XII

The following acetophenones are prepared by the noted methods from the carboxylic acids of Tables I or II or appropriate derivatives thereof which are obtained by the methods of Examples 277–280.

| Example No. | Method of Example | 4-(Substituted-amino)acetophenones |
|---|---|---|
| 292 | 281 | Diethyl 4-[(3-cyclohexylpentyl)amino]-benzoylmalonate |
| 293 | 282 | tert-Butyl ethyl 4-(1-cyclopent-3-enyl-methylamino)benzoylmalonate |
| 294 | 283 | Ethyl 2-[4-(cycloheptylmethylamino)-benzoyl]acetoacetate |
| 295 | 284 | Ethyl 4-[3-methyl-3-(4-methylcyclohex-3-enyl)propylamino]benzoylacetate |
| 296 | 285 | 4-[3-(Cyclohex-3-enyl)propylamino]-benzoylacetic acid |
| 297 | 286 | 4-[3-(3-Cyclohexenyl)propylamino]-2-(methylsulfonyl)acetophenone |
| 298 | 287 | 4'-(Cyclonon-3-enylamino)-2-(phenylsulfonyl)acetophenone |
| 299 | 288 | 4'-[(5-Ethylcyclohex-3-enyl)-methylamino]-2-(phenylsulfinyl)-acetophenone |
| 300 | 289 | 3'-[4-(4-Isopropylcyclohex-2-enylamino)-benzoyl]-2,4-pentanedione |
| 301 | 290 | Methyl 3-[4-(2-cylooct-1-enylethylamino)benzoyl]propionate |
| 302 | 291 | 3-[4-(2-Methyl-6-methylcycloheptyl-amino)benzoyl]propionic acid |

EXAMPLE 303

Preparation of 4-(2-methylcyclopentylmethyl)amino]benzonitrile

4-Aminobenzonitrile (11.8 g.) and 1-iodomethyl-2-methylcyclopentane (16.3 g.) are dissolved in hexamethylphosphoramide (100 ml.) and heated under nitrogen in an oil bath maintained at 120° C. for 22 hours. The reaction mixture is cooled to room temperature and water (100 ml.) is added gradually. The mixture is then chilled in an ice bath. The precipitate separated is filtered, washed thoroughly with water, and dried. It is then washed repeatedly with hexane and dried. Recrystallization from ether-hexane affords 4-(2-methylcyclopentylmethylamino)benzonitrile as pale yellow crystals.

EXAMPLE 304

Preparation of 4-(cyclohex-3-enylamino)benzaldehyde

Di-isobutylaluminum hydride (54 ml., 25% solution in toluene) is added with stirring to a solution of 12.1 g. of 4-(cyclohex-3-enylamino)benzonitrile under a nitrogen atmosphere. After addition is completed, the solution stirred for one hour. A solution of methanol in toluene (50 ml., 1:1) is added over 30 minutes and the mixture is poured into 500 ml. vigorously stirred ice-cold 50% aqueous sulfuric acid. The mixture is filtered and the organic layer separated. The aqueous solution is extracted twice with toluene (100 ml.) and the combined organic layers are washed with acqueous sodium bicarbonate, dried over magnesium sulfate, decolorized with charcoal, filtered and evaporated in vacuo to give a light yellow crystalline solid. The product is recrystallized from dichloromethane/hexane giving colorless needles.

TABLE XIII

The following 4-[(cycloalkyl or cycloalkenyl substituted)amino, alkylamino or alkenylamino]benzonitriles are prepared by the method of Example 303.

| Example No. | 4-(Substituted-amino)benzonitrile |
|---|---|
| 305 | 4-(Cyclohex-3-enylamino)benzonitrile |
| 306 | 4-(Cyclohexylmethylamino)benzonitrile |
| 307 | 4-(2-Methyl-6-methylenylcycloheptylamino) benzonitrile |
| 308 | 4-[(4-Cyclopropyl)but-3-enylamino] benzonitrile |
| 309 | 4-[1-(3-Butenyl)-2-methylcycloheptylamino] benzonitrile |

TABLE XIII-continued

The following 4-[(cycloalkyl or cycloalkenyl substituted)amino, alkylamino or alkenylamino]benzonitriles are prepared by the method of Example 303.

| Example No. | 4-(Substituted-amino)benzonitrile |
|---|---|
| 310 | 4-[4-(2-Decahydronaphthyl)butylamino]benzonitrile |
| 311 | 4-[5-(1-Cyclopentenyl)pentyamino]benzonitrile |

TABLE XIV

The following 4-[(cycloalkyl or cycloalkenyl substituted amino, alkylamino or alkenylamino]benzaldehydes are prepared from the corresponding benzonitriles of Table XIII by the method of Example 304.

| Example No. | 4-(Substituted-amino)benzaldehydes |
|---|---|
| 312 | 4-(Cyclohex-3-enylamino)benzaldehyde |
| 313 | 4-(Cyclohexylmethylamino)benzaldehyde |
| 314 | 4-(2-Methyl-6-methylenylcycloheptylamino) benzaldehyde |
| 315 | 4-[(4-Cyclopropyl)but-3-enylamino] benzaldehyde |
| 316 | 4-[1-(3-Butenyl)-2-methylcycloheptylamino] benzaldehyde |
| 317 | 4-[4-(2-Decahydronaphthyl)butylamino benzaldehyde |
| 318 | 4-[5-(1-Cyclopentenyl)pentylamino]benzaldehyle |

EXAMPLE 319

Preparation of 2,3-dihydroxypropyl 4-(2-cyclohexylethylaminophenylacetate

A solution of 7.34 g. of 4-(2-cyclohexylethylamino)-phenylacetic acid, 4.80 g. of 25% aqueous sodium hydroxide, and 12.6 g. of 3-iodo-1,2-propanediol in 50 ml. of hexamethylphosphoramide is stirred for 24 hours at ambient temperature, diluted with 100 ml. of ether and stirred for 5 days at ambient temperature. The mixture is treated with water and extracted with ether. The dried extracts are evaporated to yield 2,3-dihydroxypropyl 4-(2-cyclohexylethylaminophenylacetic acid.

EXAMPLE 320

Preparation of methyl 4-(2-cyclohexylethylamino)phenylacetate

A solution of 20.7 g. of 4-(2-cyclohexylethylamino)-phenylacetic acid in 25 ml. of hexamethylphosphoramide is added to a stirred mixture of 0.800 g. of sodium hydride (57% in mineral oil) and 25 ml. of hexamethylphosphoramide. The solution which forms after one hour is treated with 11.0 g. of methyl iodide and is then stirred at 25° C. for 18 hours. Dilution with water followed by filtration affords a white solid which is crystallized from ethanol to yield methyl 4-(2-cyclohexylethylamino)phenylacetate.

EXAMPLE 321

Preparation of 3-hydroxypropyl 4-(2-cyclohexylethylamino)phenylacetate

A mixture of 2.25 g. of methyl 4-(2-cyclohexylethylamino)phenylacetate, 280 mg. of 1,3-propanediol and 1.37 g. p-toluenesulfonic acid is heated at 180° C. for 18 hours and then is partitioned between ether and 3% aqueous sodium carbonate solution. The ether layer is separated, dried, and evaporated to yield 3-hydroxypropyl 4-(2-cyclohexylethylamino)phenylacetate.

EXAMPLE 322

Preparation of 2-ethoxyethyl 4-(cyclohex-2-enylmethylamino)phenylacetate

A solution of 11.8 g. of 4-(cyclohex-2-enylmethylamino)phenylacetic acid, 1.00 g. of 2-ethoxyethanol and 5.35 ml. of boron trifluoride etherate in 200 ml. toluene is stirred under reflux for 48 hours. The solution is treated with an additional 5.35 ml. of boron trifluoride etherate and refluxing is continued for 120 hours. Dilution with water and methylene chloride followed by filtration affords 2-ethoxyethyl 4-(cyclohex-2-enylmethylamino)phenylacetate.

EXAMPLE 323

Preparation of methyl 4-(2-cyclohexylhept-3-enylamino)hydrocinnamate

A solution of 50.5 g. of 4-(2-cyclohexylhept-3-enylamino)hydrocinnamic acid and 34.4 ml. of boron trifluoride etherate in 200 ml. of methanol is stirred under reflux for 44 hours, allowed to cool, and poured into 1.20 liters of ice-cold 5% aqueous sodium carbonate solution. The white solid is collected by filtration and recrystallized from benzene-ethanol to yield methyl 4-(2-cyclohexylhept-3-enylamino)hydrocinnamate.

EXAMPLE 324

Preparation of 1-(methoxycarbonyl)propyl 4-(cyclohex-3-enylmethylamino)hydrocinnamate To a solution of 10.0 g. 4-(cyclohex-3-enylmethylamino)hydrocinnamoyl chloride hydrochloride in 200 ml. methylene chloride is added dropwise a solution of 3 g. methyl 2-hydroxybutyrate and 5 g. triethylamine in 100 ml. ether. After 17 hours stirring at room temperature, the precipitate is collected and washed with several portions of ether. The ether solution is washed with water, dried and evaporated to yield 1-(methoxycarbonyl)propyl 4-(cyclohex-3-enylmethylamino)hydrocinnamate as a white solid.

EXAMPLE 325

Preparation of 1-(ethoxycarbonyl)ethyl 4-(2-cyclohexylethylamino)phenylacetate

To a warm mixture of 7 g. sodium 4-(2-cyclohexylethylamino)phenylacetate in 100 ml. ethanol is added 4.7 g. ethyl 2-tosyloxypropionate. After 17 hours at reflux, the cooled solution is diluted with an equal volume of water and the resultant precipitate is filtered. After washing with cold ethanol and drying, the product is crystallized from acetonitrile to yield 1-(ethoxycarbonyl)ethyl 4-(2-cyclohexylethylamino)phenylacetate as colorless crystals.

EXAMPLE 326

Preparation of 1-carboxyethyl 4-(2-cyclohexylethylamino)phenylacetate

A flask containing 10.0 g. 4-(2-cyclohexylethylamino)phenylacetic acid, 3.3 g. lactic acid, 500 mg. toluenesulfonic acid and 500 ml. toluene equipped with a Soxhlet extractor charged with activated 4 A Linde molecular sieves. The solution is refluxed for 24 hours during which time the Soxhlet extractor is charged twice more with fresh sieves. The hot solution is filtered and left to cool, whereupon 1-carboxyethyl 4-(2-cyclohexylethylamino)phenylacetate separates as off-white crystals.

EXAMPLE 327

Preparation of diethyl O-[4-(2-cyclohexylethylamino)phenylacetyl]tartrate

A mixture of 4-[N-trifluoroacetyl-(2-cyclohexylethylamino)]phenylacetyl chloride and 1.2 g. triethylamine in 100 ml. warm ether is treated with 2.5 g. diethyl tartrate and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields diethyl O-[4-(2-cyclohexylethylamino)phenylacetyl]tartrate as a white, crystalline solid.

EXAMPLE 328

Preparation of O-[4-(2-cyclohexylethylamino)phenylacetyl]malic acid

A warm solution of 4-[N-carbobenzyloxy-(2-cyclohexylethylamino)phenylacetyl]chloride and 1.3 g. triethylamine in 100 ml. ether is treated with 2 g. malic acid. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% palladium-on-carbon at 50 psi until hydrogen uptake stops. The catalyst is filtered, and the solution is evaporated. The residue is crystallized from acetic acid to yield O-[4-(2-cyclohexylethylamino)phenylacetyl]malic acid.

EXAMPLE 329

Preparation of 2-(ethoxycarbonyl)vinyl 4-(2-cyclohexylethylamino)phenylacetate To a mixture containing 4.3 g. 1-[4-(N-t-butyloxycarbonyl-2-cyclohexylethylamino)phenylacetyl]imidazole 50 ml. 5 N sodium hydroxide is added 3 g. ethyl 2-formyl acetate. The solution is vigorously stirred for 24 hours. The layers are separated, and the chloroform solution is washed once with 50 ml. 1 N sodium hydroxide. The solvent is evaporated and the residue is heated for 30 minutes at 40° C. in 50 ml. anhydrous trifluoroacetic acid. The solvent is again evaporated and the oil is crystallized from acetone to yield light yellow crystals of 2-(ethoxycarbonyl)vinyl 4-(2-cyclohexylethylamino)phenylacetate.

TABLE XV

The following esters are prepared by the methods shown from the carboxylic acids of Tables I, II, IV, VI, VIII and X or appropriate derivatives thereof obtained by the methods of Examples 276–280.

| Example No. | Method of Example | Ester |
|---|---|---|
| 330 | 319 | 2,3-Dihydroxypropyl 4-(1-cyclopentylethylamino)phenylacetate |
| 331 | 319 | 2,3-Dihydroxypropyl 4-(cyclohex-2-enylmethylamino)hydrocinnamate |
| 332 | 319 | 2,3-Dihydroxypropyl 4-(cyclooct-4-enylamino)cinnamate |
| 333 | 319 | 2,3-Dihydroxypropyl 4-(1-allyl-2-methylcyclohexylamino)phenyl propiolate |
| 334 | 319 | 2,3-Dihydroxypropyl 4-(4-cyclopentylbut-2-enylamino)butyrate |
| 335 | 320 | Methyl 4-(cyclooctylmethylamino)phenylacetate |
| 336 | 320 | Methyl 4-(cyclooct-2-enylamino)hydrocinnamate |
| 337 | 320 | Methyl 4-(2-butylcyclopent-2-enylamino)cinnamate |
| 338 | 320 | Methyl 4-(cyclohex-3-enylamino)phenylpropiolate |
| 339 | 320 | Methyl 4-[4-(cyclohexylmethylamino)phenyl]butyric acid |
| 340 | 321 | 2-Hydroxypropyl 4-(3-cyclopentylpropylamino)phenylacetate |
| 341 | 321 | 4-Hydroxybutyl 4-[(2-cyclohexyl)hex-4-enylamino]hydrocinnamate |
| 342 | 321 | 2-Hydroxypropyl 4-(cyclopropylmethylamino)cinnamate |
| 343 | 321 | 3-Hydroxypropyl 4-(cyclohexylmethylamino)phenylpropiolate |
| 344 | 321 | 2-Hydroxyethyl 4-[(2-methylcyclohexylmethylamino)butyrate |
| 345 | 322 | 2-Methoxyethyl 4-(cyclohex-2-enylmethylamino)phenylacetate |
| 346 | 322 | 2-Ethoxyethyl 4-(1-cyclopentylbut-2-enylamino)propiolate |
| 347 | 323 | Methyl 4-(2-cyclopentylhexylamino)hydrocinnamate |
| 348 | 323 | Methyl 4-(4-cycloheptylpentylamino)cinnamate |
| 349 | 324 | 1-Methoxycarbonylpropyl 4-(cyclohexylmethylamino)hydrocinnamate |
| 350 | 324 | 1-Ethoxycarbonylpropyl 4-[2-(cyclobutylpropyl)amino]phenylpropiolate |
| 351 | 325 | 1-Ethoxycarbonylethyl 4-(cyclopentylmethylamino)phenylpropiolate |
| 352 | 326 | 1-Carboxyethyl 4-(2-cyclohexylpropylamino)phenylacetate |
| 353 | 326 | 1-Carboxyethyl 4-[2-(2-ethylcyclohexyl)ethylamino]cinnamate |
| 354 | 326 | 1-Carboxybutyl 4-(2-cyclopentylethylamino)propiolate |
| 355 | 326 | 1-Carboxyethyl 4-[4-(cyclopentylmethylamino)phenyl]butyrate |
| 356 | 327 | 3-Pyridyl 4-(cyclooctylmethylamino)cinnamate |
| 357 | 328 | O—[4-(Cyclohexylmethylamino)benzoylmalic acid |
| 358 | 328 | O—[-4-(4-cyclopentylbut-3-ynyl)benzoyl]malic acid |
| 359 | 329 | 2-(Ethoxycarbonyl)vinyl 4-(cyclohexylmethylamino)hydrocinnamate |
| 360 | 329 | 2-(Ethoxycarbonyl)vinyl 4-(3-cyclopentylpropylamino)cinnamate |
| 361 | 329 | 2-(Ethoxycarbonyl)vinyl 4-(cyclohex-3-enylmethylamino)propiolate |
| 362 | 329 | 2-(Ethoxycarbonyl)vinyl 4-[4-(1-cycloheptylpent-2-enylamino)butyrate |

TABLE XVI

The following compounds are prepared from the carboxylic acids which may be prepared from the corresponding nitriles and aldehydes which are obtained by the methods of Examples 303 and 304 or from appropriate acid derivatives obtained by the methods of Examples 276–280.

| Example No. | Method of Example | 4-(Substituted-amino)compounds |
|---|---|---|
| 363 | 281 | Diethyl 4-(cyclooctylmethylamino)benzoylmalonate |
| 364 | 282 | tert-Butyl ethyl 4-(2-cyclopentylbutylamino)benzoylmalonate |
| 365 | 283 | Ethyl 2-[4-(cyclopentylbut-2-enyl-aminobenzoyl]acetoacetate |
| 366 | 284 | Ethyl 4-[2-(2-methylcyclohexyl)ethylamino]benzoylacetate |
| 367 | 285 | 4-(Cyclobutylmethylamino)benzoylacetic acid |

TABLE XVI-continued

The following compounds are prepared from the carboxylic acids which may be prepared from the corresponding nitriles and aldehydes which are obtained by the methods of Examples 303 and 304 or from appropriate acid derivatives obtained by the methods of Examples 276–280.

| Example No. | Method of Example | 4-(Substituted-amino)compounds |
|---|---|---|
| 368 | 290 | Methyl 3-[4-(2-cyclohexylethyl amino)benzoyl]propionate |
| 369 | 291 | 3-[4-(2-Cyclooct-1-enylethylamino)-benzoyl]propionic acid |

I claim:
1. The compound p-[(cyclohexyl)methylamino]cinnamic acid.
2. The compound 3-pyridyl p-[7-(cyclopentyl)heptylamino]cinnamate.
3. The compound 4-[(cyclopentyl)methylamino]phenylpropiolic acid.
4. The compound p-[4-(propyl)cyclohexylamino]cinnamic acid.
5. The compound p-[1-(cyclohept-1-enyl)ethylamino]cinnamic acid.
6. The compound p-(3,7-dimethylcyclohept-3-enylamino)cinnamic acid.

* * * * *